US011814424B2

(12) United States Patent
Iwamoto et al.

(10) Patent No.: US 11,814,424 B2
(45) Date of Patent: Nov. 14, 2023

(54) ANTI-VARICELLA-ZOSTER VIRUS ANTIBODY, IMMUNOLOGICAL MEASUREMENT METHOD, AND IMMUNOLOGICAL MEASUREMENT DEVICE

(71) Applicant: TANAKA KIKINZOKU KOGYO K.K., Tokyo (JP)

(72) Inventors: Hisahiko Iwamoto, Kanagawa (JP); Keita Suzuki, Kanagawa (JP); Tetsuo Tomiyama, Tokyo (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 211 days.

(21) Appl. No.: 17/240,580

(22) Filed: Apr. 26, 2021

(65) Prior Publication Data

US 2021/0332109 A1 Oct. 28, 2021

(30) Foreign Application Priority Data

Apr. 27, 2020 (JP) ................................ 2020-078713

(51) Int. Cl.
*A61K 39/42* (2006.01)
*C07K 16/08* (2006.01)
*G01N 33/569* (2006.01)

(52) U.S. Cl.
CPC ..... *C07K 16/088* (2013.01); *G01N 33/56994* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 2010/0047247 A1 | 2/2010 | Shiraki et al. | |
| 2015/0166639 A1 | 6/2015 | Shiraki et al. | |
| 2018/0372745 A1 | 12/2018 | Suzuki et al. | |

FOREIGN PATENT DOCUMENTS

| | | | | |
|---|---|---|---|---|
| CN | 105542004 | A | * | 5/2016 |
| JP | 2008-253188 | A | | 10/2008 |
| JP | 5279504 | B2 | | 9/2013 |
| WO | 2004/1103690 | A1 | * | 12/2004 |
| WO | 2008/022295 | | * | 5/2008 |
| WO | 2008/140653 | A2 | * | 11/2008 |
| WO | WO-2017-090744 | A1 | | 6/2017 |
| WO | 2018/195301 | | * | 10/2018 |
| WO | 2018/217058 | A1 | * | 11/2018 |

* cited by examiner

*Primary Examiner* — Jennifer E Graser
(74) *Attorney, Agent, or Firm* — Foley & Lardner LLP

(57) ABSTRACT

An object of the present invention is to provide a means for rapidly diagnosing infection with VZV. The present invention relates to an antibody against VZVgE or an antibody fragment thereof, and an immunological measurement method and an immunological measurement device using the antibody or the antibody fragment thereof, etc.

2 Claims, 3 Drawing Sheets

Specification includes a Sequence Listing.

[FIG. 1]
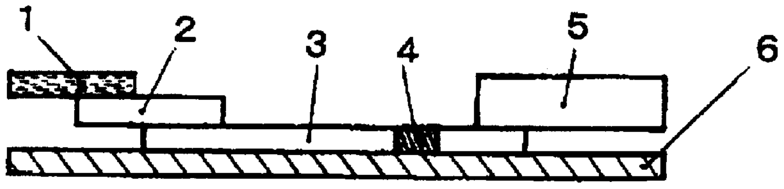

[FIG. 2]
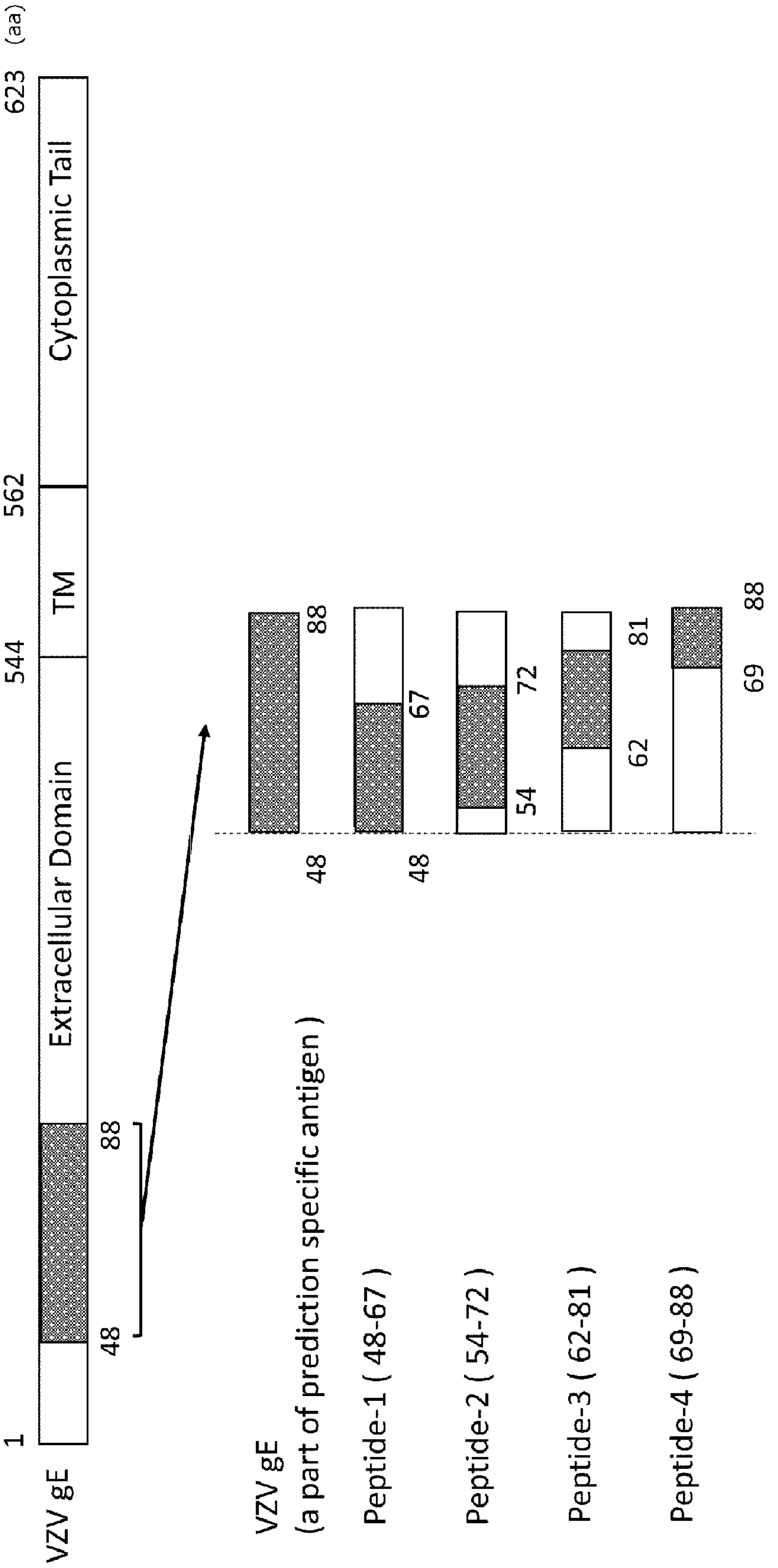

[FIG. 3]
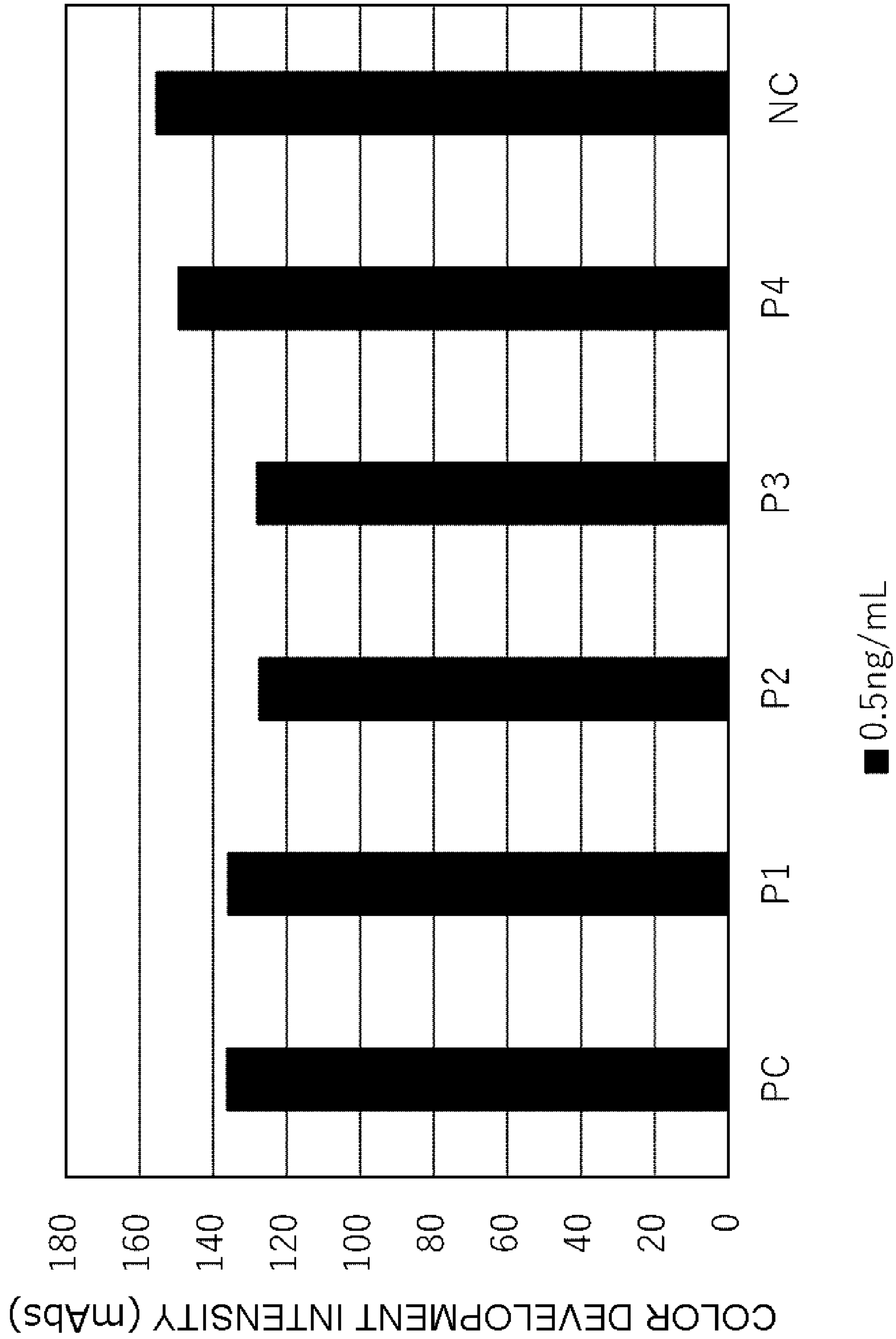

SEQUENCE LISTING

```
<160> NUMBER OF SEQ ID NOS: 30

<210> SEQ ID NO 1
<211> LENGTH: 623
<212> TYPE: PRT
```

```
<213> ORGANISM: Varicella zoster

<400> SEQUENCE: 1

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400
```

-continued

```
Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Tyr Arg Val Asp Lys Ser Pro Tyr
                565                 570                 575

Asn Gln Ser Met Tyr Tyr Ala Gly Leu Pro Val Asp Asp Phe Glu Asp
            580                 585                 590

Ser Glu Ser Thr Asp Thr Glu Glu Glu Phe Gly Asn Ala Ile Gly Gly
        595                 600                 605

Ser His Gly Gly Ser Ser Tyr Thr Val Tyr Ile Asp Lys Thr Arg
    610                 615                 620


<210> SEQ ID NO 2
<211> LENGTH: 544
<212> TYPE: PRT
<213> ORGANISM: Varicella zoster

<400> SEQUENCE: 2

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160
```

-continued

```
Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540
```

<210> SEQ ID NO 3
<211> LENGTH: 41
<212> TYPE: PRT
<213> ORGANISM: Varicella zoster

<400> SEQUENCE: 3

Asn Ser Val Tyr Glu Pro Tyr Tyr His Ser Asp His Ala Glu Ser Ser
1 5 10 15

Trp Val Asn Arg Gly Glu Ser Ser Arg Lys Ala Tyr Asp His Asn Ser
20 25 30

Pro Tyr Ile Trp Pro Arg Asn Asp Tyr
35 40

<210> SEQ ID NO 4
<211> LENGTH: 20
<212> TYPE: PRT
<213> ORGANISM: Varicella zoster

<400> SEQUENCE: 4

Asn Ser Val Tyr Glu Pro Tyr Tyr His Ser Asp His Ala Glu Ser Ser
1 5 10 15

Trp Val Asn Arg
20

<210> SEQ ID NO 5
<211> LENGTH: 19
<212> TYPE: PRT
<213> ORGANISM: Varicella zoster

<400> SEQUENCE: 5

Tyr Tyr His Ser Asp His Ala Glu Ser Ser Trp Val Asn Arg Gly Glu
1 5 10 15

Ser Ser Arg

<210> SEQ ID NO 6
<211> LENGTH: 20
<212> TYPE: PRT
<213> ORGANISM: Varicella zoster

<400> SEQUENCE: 6

Ser Ser Trp Val Asn Arg Gly Glu Ser Ser Arg Lys Ala Tyr Asp His
1 5 10 15

Asn Ser Pro Tyr
20

<210> SEQ ID NO 7
<211> LENGTH: 20
<212> TYPE: PRT
<213> ORGANISM: Varicella zoster

<400> SEQUENCE: 7

Glu Ser Ser Arg Lys Ala Tyr Asp His Asn Ser Pro Tyr Ile Trp Pro
1 5 10 15

Arg Asn Asp Tyr
20

<210> SEQ ID NO 8
<211> LENGTH: 8
<212> TYPE: PRT
<213> ORGANISM: Mus musculus

<400> SEQUENCE: 8

Gly Tyr Thr Phe Thr Asp Tyr Asn
1 5

<210> SEQ ID NO 9

-continued

<211> LENGTH: 9
<212> TYPE: PRT
<213> ORGANISM: Mus musculus

<400> SEQUENCE: 9

Glu Ile Asn Pro Glu Asn Gly Gly Thr
1 5

<210> SEQ ID NO 10
<211> LENGTH: 8
<212> TYPE: PRT
<213> ORGANISM: Mus musculus

<400> SEQUENCE: 10

Ala Arg Ser Pro Trp Phe Thr Tyr
1 5

<210> SEQ ID NO 11
<211> LENGTH: 6
<212> TYPE: PRT
<213> ORGANISM: Mus musculus

<400> SEQUENCE: 11

Thr Asp Ile Gly Asp Asp
1 5

<210> SEQ ID NO 12
<211> LENGTH: 3
<212> TYPE: PRT
<213> ORGANISM: Mus musculus

<400> SEQUENCE: 12

Glu Gly Asn
1

<210> SEQ ID NO 13
<211> LENGTH: 8
<212> TYPE: PRT
<213> ORGANISM: Mus musculus

<400> SEQUENCE: 13

Leu Gln Ser Asp Asn Leu Pro His
1 5

<210> SEQ ID NO 14
<211> LENGTH: 9
<212> TYPE: PRT
<213> ORGANISM: Mus musculus

<400> SEQUENCE: 14

Gly Tyr Ser Ile Thr Ser Asp Tyr Ala
1 5

<210> SEQ ID NO 15
<211> LENGTH: 7
<212> TYPE: PRT
<213> ORGANISM: Mus musculus

<400> SEQUENCE: 15

Ile Ser Tyr Ser Gly Asn Ser
1 5

<210> SEQ ID NO 16
<211> LENGTH: 10
<212> TYPE: PRT

<213> ORGANISM: Mus musculus

<400> SEQUENCE: 16

Ala Arg Asp Gly Ser Arg Gly Phe Asp Tyr
1 5 10

<210> SEQ ID NO 17
<211> LENGTH: 12
<212> TYPE: PRT
<213> ORGANISM: Mus musculus

<400> SEQUENCE: 17

Gln Ser Leu Leu Tyr Ser Ser Asn Gln Lys Asn Tyr
1 5 10

<210> SEQ ID NO 18
<211> LENGTH: 3
<212> TYPE: PRT
<213> ORGANISM: Mus musculus

<400> SEQUENCE: 18

Trp Ala Ser
1

<210> SEQ ID NO 19
<211> LENGTH: 9
<212> TYPE: PRT
<213> ORGANISM: Mus musculus

<400> SEQUENCE: 19

Gln Gln Tyr Tyr Tyr Tyr Pro Pro Thr
1 5

<210> SEQ ID NO 20
<211> LENGTH: 115
<212> TYPE: PRT
<213> ORGANISM: Mus musculus

<400> SEQUENCE: 20

Glu Val Gln Leu Glu Glu Ser Gly Pro Glu Leu Val Lys Pro Gly Ala
1 5 10 15

Ser Val Lys Ile Pro Cys Lys Ala Ser Gly Tyr Thr Phe Thr Asp Tyr
20 25 30

Asn Met Asp Trp Val Lys Gln Asn His Gly Lys Ser Leu Glu Trp Ile
35 40 45

Gly Glu Ile Asn Pro Glu Asn Gly Gly Thr Ile Tyr Asn Gln Thr Phe
50 55 60

Lys Gly Lys Ala Thr Leu Thr Val Asp Lys Ser Ser Ser Thr Ala Tyr
65 70 75 80

Met Glu Leu Arg Ser Leu Thr Ser Glu Asp Thr Ala Val Tyr Tyr Cys
85 90 95

Ala Arg Ser Pro Trp Phe Thr Tyr Trp Gly Gln Gly Thr Leu Val Thr
100 105 110

Val Ser Ala
115

<210> SEQ ID NO 21
<211> LENGTH: 106
<212> TYPE: PRT
<213> ORGANISM: Mus musculus

<400> SEQUENCE: 21

```
Asp Ile Val Leu Thr Gln Thr Thr Ala Ser Leu Ser Met Ala Ile Gly
1               5                   10                  15

Glu Ile Val Thr Ile Arg Cys Ile Thr Ser Thr Asp Ile Gly Asp Asp
            20                  25                  30

Met Asn Trp Tyr Gln Gln Lys Pro Gly Glu Pro Pro Lys Phe Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Val Glu Asn Ile Leu Ser
65                  70                  75                  80

Glu Asp Val Ala Asp Tyr Tyr Cys Leu Gln Ser Asp Asn Leu Pro His
                85                  90                  95

Val Arg Leu Gly Asp Lys Val Gly Asn Lys
            100                 105


<210> SEQ ID NO 22
<211> LENGTH: 117
<212> TYPE: PRT
<213> ORGANISM: Mus musculus

<400> SEQUENCE: 22

Glu Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Asn Ser Ser Tyr Asn Pro Ser Leu
    50                  55                  60

Lys Ser Arg Ile Ser Phe Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Asp Gly Ser Arg Gly Phe Asp Tyr Trp Gly Gln Gly Thr Thr
            100                 105                 110

Leu Thr Val Ser Ser
        115


<210> SEQ ID NO 23
<211> LENGTH: 113
<212> TYPE: PRT
<213> ORGANISM: Mus musculus

<400> SEQUENCE: 23

Asp Ile Val Leu Thr Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95
```

```
Tyr Tyr Tyr Tyr Pro Pro Thr Phe Gly Ala Gly Thr Lys Leu Glu Leu
            100                 105                 110

Lys


<210> SEQ ID NO 24
<211> LENGTH: 346
<212> TYPE: DNA
<213> ORGANISM: Mus musculus

<400> SEQUENCE: 24

gaagttcagc tggaggagtc tggacctgag ctggtgaagc ctggggcttc agtgaagatc     60

ccctgcaagg cttctggata cacattcact gactacaaca tggactgggt gaaacaaaac    120

catggaaaga gccttgagtg gattggagaa attaatcctg agaatggtgg tactatctac    180

aaccagacgt tcaagggcaa ggccacattg actgtagaca agtcctccag cacagcctac    240

atggagctcc gcagcctgac atctgaggac acagcagtct actactgtgc aagatccccc    300

tggtttactt actggggcca agggactctg gtcactgtct ctgcag                   346


<210> SEQ ID NO 25
<211> LENGTH: 320
<212> TYPE: DNA
<213> ORGANISM: Mus musculus

<400> SEQUENCE: 25

gatattgtgc tgacacaaac tacagcatcc ctgtccatgg ctataggaga aatagtcacc     60

atcagatgca taaccagcac tgatattggt gatgatatga actggtacca gcagaagcca    120

ggggaacctc ctaagttcct tatttcagaa ggcaacactc ttcgtcctgg agtcccatcc    180

cgattctcca gcagtggcta tggtacagat tttgttttta cagttgaaaa catactctca    240

gaagatgttg cagattacta ctgtttgcaa agtgataact tgcctcacgt tcggctcggg    300

gacaaagttg gaaataaaac                                                320


<210> SEQ ID NO 26
<211> LENGTH: 352
<212> TYPE: DNA
<213> ORGANISM: Mus musculus

<400> SEQUENCE: 26

gaagttcagc tgcaggagtc tggacctggc ctggtgaaac cttctcagtc tctgtccctc     60

acctgcactg tcactggcta ctcaatcacc agtgattatg cctggaactg gatccggcag    120

tttccaggaa acaaactgga gtggatgggc tacataagct acagtggtaa ctctagctac    180

aacccatctc tcaaaagtcg aatctctttc actcgagaca catccaagaa ccagttcttc    240

ctgcagttga attctgtgac tactgaggac acagccacat attactgtgc acgagacggt    300

agtcgcggct ttgactactg gggccaaggc accactctca cagtctcctc ag            352


<210> SEQ ID NO 27
<211> LENGTH: 340
<212> TYPE: DNA
<213> ORGANISM: Mus musculus

<400> SEQUENCE: 27

gatattgtgc tgacacagtc tccatcctcc ctagctgtgt cagttggaga gaaggttact     60

atgagctgca agtccagtca gagcctttta tatagtagca atcaaaagaa ctacttggcc    120

tggtaccagc agaaaccagg gcagtctcct aaactgctga tttactgggc atccactagg    180
```

gaatctgggg tccctgatcg cttcacaggc agtggatctg ggacagattt cactctcacc 240
atcagcagtg tgaaggctga agacctggca gtttattact gtcagcaata ttattactat 300
cctcctacgt tcggtgctgg gaccaagctg gagctgaaac 340

<210> SEQ ID NO 28
<211> LENGTH: 32
<212> TYPE: DNA
<213> ORGANISM: Artificial Sequence
<220> FEATURE:
<223> OTHER INFORMATION: Synthetic oligonucleotides used as a primer
<220> FEATURE:
<221> NAME/KEY: misc_feature
<222> LOCATION: (13)..(13)
<223> OTHER INFORMATION: s is c or g
<220> FEATURE:
<221> NAME/KEY: misc_feature
<222> LOCATION: (15)..(15)
<223> OTHER INFORMATION: r is a or g
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (19)..(19)
<223> OTHER INFORMATION: m is a or c
<220> FEATURE:
<221> NAME/KEY: misc_feature
<222> LOCATION: (25)..(25)
<223> OTHER INFORMATION: s is c or g
<220> FEATURE:
<221> NAME/KEY: misc_feature
<222> LOCATION: (28)..(28)
<223> OTHER INFORMATION: s is c or g

<400> SEQUENCE: 28
cttccggaat tcsargtnma gctgsagsag tc 32

<210> SEQ ID NO 29
<211> LENGTH: 35
<212> TYPE: DNA
<213> ORGANISM: Artificial Sequence
<220> FEATURE:
<223> OTHER INFORMATION: Synthetic oligonucleotides used as a primer
<220> FEATURE:
<221> NAME/KEY: misc_feature
<222> LOCATION: (13)..(13)
<223> OTHER INFORMATION: s is c or g
<220> FEATURE:
<221> NAME/KEY: misc_feature
<222> LOCATION: (15)..(15)
<223> OTHER INFORMATION: r is a or g
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (19)..(19)
<223> OTHER INFORMATION: m is a or c
<220> FEATURE:
<221> NAME/KEY: misc_feature
<222> LOCATION: (25)..(25)
<223> OTHER INFORMATION: s is c or g
<220> FEATURE:
<221> NAME/KEY: misc_feature
<222> LOCATION: (28)..(28)
<223> OTHER INFORMATION: s is c or g
<220> FEATURE:
<221> NAME/KEY: misc_feature
<222> LOCATION: (33)..(33)
<223> OTHER INFORMATION: w is a or t -continued

```
<400> SEQUENCE: 29

cttccggaat tcsargtnma gctgsagsag tcwgg                             35


<210> SEQ ID NO 30
<211> LENGTH: 36
<212> TYPE: DNA
<213> ORGANISM: Artificial Sequence
<220> FEATURE:
<223> OTHER INFORMATION: Synthetic oligonucleotides used as a primer

<400> SEQUENCE: 30

ggaagatcta tagacagatg ggggtgtcgt tttggc                            36
```

ANTI-VARICELLA-ZOSTER VIRUS ANTIBODY, IMMUNOLOGICAL MEASUREMENT METHOD, AND IMMUNOLOGICAL MEASUREMENT DEVICE

CROSS-REFERENCE TO RELATED APPLICATIONS

This application is based on and claims priority under 35 USC 119 from Japanese Patent Application No. 2020-078713 filed on Apr. 27, 2020, the contents of which are incorporated herein by reference.

TECHNICAL FIELD

The present invention relates to an anti-varicella-zoster virus antibody or an antibody fragment thereof for detecting varicella-zoster virus, and an immunological measurement method and an immunological measurement device using the antibody or the antibody fragment thereof.

BACKGROUND ART

Varicella-zoster virus (VZV) is a virus which belongs to the α-herpesvirinae and has a linear double-stranded DNA composed of a base sequence of about 125 kbp. This virus causes varicella in the initial infection in humans and remains latent in satellite cells around nerve cells in an inactive stage after healing. When immunocompetence is reduced due to some causes, the virus is reactivated to cause zoster. When a human in an immunosuppressed state (who uses an immunosuppressive agent, or who has an underlying disease such as malignant tumor or immunodeficiency) is initially infected with VZV or VZV is reactivated, severe conditions may occur, and sometimes deadly conditions may occur. Therefore, establishment of a rapid diagnostic method for performing an early treatment has been awaited.

Japanese Patent No. 5279504 discloses a preventive or therapeutic agent for a neurological disease using an antibody which recognizes a varicella-zoster virus immediate-early protein IE62 and also crossreacts with a brain-derived neurotrophic factor as a means for prevention or treatment of nerve pain or the like after zoster.

JP-A-2008-253188 discloses an inhibitor of endocytosis-dependent DNA uptake which enhances the function of a DNase X protein, and discloses a method for indirectly predicting a pathological condition caused by varicella-zoster virus or the like using human DNase X as an antigen.

SUMMARY OF THE INVENTION

However, the method described in Japanese Patent No. 5279504 is a method for detecting the cause of nerve pain induced by VZV or treating nerve pain, and is not a method for specifically detecting VZV. Further, the method described in JP-A-2008-253188 is also not a method for directly detecting VZV itself, but is a method for indirectly predicting a pathological condition using human DNase X as an antigen.

In this manner, a method for specifically detecting VZV has not been established so far, and infection with VZV could not be diagnosed rapidly.

Therefore, aspect of non-limiting embodiments of the present disclosure relates to an object of the present invention is to provide a means for diagnosing infection with VZV rapidly.

VZV has varicella-zoster virus glycoprotein E (hereinafter also referred to as "VZVgE") which is a glycoprotein and has a function to capture an immunoglobulin G Fc region. This VZVgE has an about 50% homology in the amino acid sequence with glycoprotein E (gE) of the other α-herpesviruses (for example, HSV, BHV, FeHV, etc.), and the gE proteins of these viruses have similar functions and structures.

The present inventors conducted intensive studies by focusing on the above-mentioned VZVgE as a means for directly detecting VZV, and as a result, they found that an antibody, which recognizes VZVgE, and in which complementarity determining regions (hereinafter abbreviated as CDRs) 1 to 3 of a heavy chain variable region (hereinafter abbreviated as VH) and CDRs 1 to 3 of a light chain variable region (hereinafter abbreviated as VL) each contain a specific amino acid sequence, does not show crossreactivity with the other α-herpesviruses and can specifically detect VZV.

Then, they found that infection of humans with VZV can be diagnosed rapidly and simply by using an immunological measurement method and an immunological measurement device using the antibody, and thus completed the present invention.

Therefore, aspect of non-limiting embodiments of the present disclosure relates to the present invention is as follows.

1. An antibody against glycoprotein E of varicella-zoster virus (hereinafter varicella-zoster virus is abbreviated as VZV, and glycoprotein E of varicella-zoster virus is abbreviated as VZVgE) or an antibody fragment thereof, wherein the antibody is any one of the following antibodies (1a) to (1c) and (2a) to (2c):

(1a) an antibody in which the amino acid sequences of complementarity determining regions (hereinafter abbreviated as CDRs) 1 to 3 of a heavy chain variable region (hereinafter abbreviated as VH) contain the amino acid sequences represented by SEQ ID NOS: 8, 9, and 10, respectively, and the amino acid sequences of CDRs 1 to 3 of a light chain variable region (hereinafter abbreviated as VL) contain the amino acid sequences represented by SEQ ID NOS: 11, 12, and 13, respectively;

(1b) an antibody which contains an amino acid sequence, in which one to three amino acid residues are deleted, substituted, added, or inserted in at least any one of the amino acid sequences of CDRs 1 to 3 of VH and CDRs 1 to 3 of VL of the antibody (1a), and has an antigen-binding activity equivalent to that of the antibody (1a);

(1c) an antibody, in which the amino acid sequences of CDRs 1 to 3 of VH of the antibody contain amino acid sequences having 80% or more homology with the amino acid sequences represented by SEQ ID NOS: 8, 9, and 10, respectively, and the amino acid sequences of CDRs 1 to 3 of VL of the antibody contain amino acid sequences having 80% or more homology with the amino acid sequences represented by SEQ ID NOS: 11, 12, and 13, respectively, and which has an antigen-binding activity equivalent to that of the antibody (1a);

(2a) an antibody in which the amino acid sequences of CDRs 1 to 3 of VH of the antibody contain the amino acid sequences represented by SEQ ID NOS: 14, 15, and 16, respectively, and the amino acid sequences of CDRs 1 to 3 of VL of the antibody contain the amino acid sequences represented by SEQ ID NOS: 17, 18, and 19, respectively;

(2b) an antibody which contains an amino acid sequence, in which one to three amino acid residues are deleted, substituted, added, or inserted in at least any one of the amino acid sequences of CDRs 1 to 3 of VH and CDRs 1 to 3 of VL of the antibody (2a), and has an antigen-binding activity equivalent to that of the antibody (2a); and (2c) an antibody, in which the amino acid sequences of CDRs 1 to 3 of VH of the antibody contain amino acid sequences having 80% or more homology with the amino acid sequences represented by SEQ ID NOS: 14, 15, and 16, respectively, and the amino acid sequences of CDRs 1 to 3 of VL of the antibody contain amino acid sequences having 80% or more homology with the amino acid sequences represented by SEQ ID NOS: 17, 18, and 19, respectively, and which has an antigen-binding activity equivalent to that of the antibody (2a).

2. The antibody or the antibody fragment thereof according to the above 1, which specifically recognizes the amino acid sequence at positions 48 to 88 in the amino acid sequence represented by SEQ ID NO: 1, and does not specifically recognize the amino acid sequence at positions 48 to 67, the amino acid sequence at positions 54 to 72, the amino acid sequence at positions 62 to 81, and the amino acid sequence at positions 69 to 88 in the amino acid sequence represented by SEQ ID NO: 1.

3. The antibody or the antibody fragment thereof according to the above 1 or 2, wherein the antibody is any one of the following antibodies (IA) to (IC) and (IIA) to (IIC):

(IA) an antibody in which the amino acid sequence of VH is the amino acid sequence represented by SEQ ID NO: 20, and the amino acid sequence of VL is the amino acid sequence represented by SEQ ID NO: 21;

(IB) an antibody which contains an amino acid sequence, in which one to three amino acid residues are deleted, substituted, added, or inserted in at least one of the amino acid sequences of VH and VL of the antibody (IA), and has an antigen-binding activity equivalent to that of the antibody (IA);

(IC) an antibody, in which the amino acid sequences of VH of the antibody contains an amino acid sequence having 80% or more homology with the amino acid sequence represented by SEQ ID NO: 20, and the amino acid sequences of VL of the antibody contains an amino acid sequence having 80% or more homology with the amino acid sequence represented by SEQ ID NO: 21, and which has an antigen-binding activity equivalent to that of the antibody (IA);

(IIA) an antibody in which the amino acid sequence of VH is the amino acid sequence represented by SEQ ID NO: 22, and the amino acid sequence of VL is the amino acid sequence represented by SEQ ID NO: 23;

(IIB) an antibody which contains an amino acid sequence, in which one to three amino acid residues are deleted, substituted, added, or inserted in at least one of the amino acid sequences of VH and VL of the antibody (IIA), and has an antigen-binding activity equivalent to that of the antibody (IIA); and (IIC) an antibody, in which the amino acid sequences of VH of the antibody contains an amino acid sequence having 80% or more homology with the amino acid sequence represented by SEQ ID NO: 22, and the amino acid sequences of VL of the antibody contains an amino acid sequence having 80% or more homology with the amino acid sequence represented by SEQ ID NO: 23, and which has an antigen-binding activity equivalent to that of the antibody (IIA).

4. An antibody against VZVgE or an antibody fragment thereof, which specifically recognizes the amino acid sequence at positions 48 to 88 in the amino acid sequence represented by SEQ ID NO: 1, and does not specifically recognize the amino acid sequence at positions 48 to 67, the amino acid sequence at positions 54 to 72, the amino acid sequence at positions 62 to 81, and the amino acid sequence at positions 69 to 88 in the amino acid sequence represented by SEQ ID NO: 1.

5. The antibody or the antibody fragment thereof according to any one of the above 1 to 4, wherein the antibody is a genetically recombinant antibody.

6. The antibody fragment according to any one of the above 1 to 5, which is an antibody fragment selected from Fab, Fab', F(ab')2, a single chain antibody (scFv), a dimerized V region (diabody), a disulfide-stabilized V region (dsFv), and a peptide including CDR.

7. An immunological measurement method, which includes using any one of the following antibodies (1a) to (1c) or an antibody fragment thereof and any one of the following antibodies (2a) to (2c) or an antibody fragment thereof are used:

(1a) an antibody in which the amino acid sequences of CDRs 1 to 3 of VH contain the amino acid sequences represented by SEQ ID NOS: 8, 9, and 10, respectively, and the amino acid sequences of CDRs 1 to 3 of VL contain the amino acid sequences represented by SEQ ID NOS: 11, 12, and 13, respectively;

(1b) an antibody which contains an amino acid sequence, in which one to three amino acid residues are deleted, substituted, added, or inserted in at least any one of the amino acid sequences of CDRs 1 to 3 of VH and CDRs 1 to 3 of VL of the antibody (1a), and has an antigen-binding activity equivalent to that of the antibody (1a);

(1c) an antibody, in which the amino acid sequences of CDRs 1 to 3 of VH of the antibody contain amino acid sequences having 80% or more homology with the amino acid sequences represented by SEQ ID NOS: 8, 9, and 10, respectively, and the amino acid sequences of CDRs 1 to 3 of VL of the antibody contain amino acid sequences having 80% or more homology with the amino acid sequences represented by SEQ ID NOS: 11, 12, and 13, respectively, and which has an antigen-binding activity equivalent to that of the antibody (1a);

(2a) an antibody in which the amino acid sequences of CDRs 1 to 3 of VH of the antibody contain the amino acid sequences represented by SEQ ID NOS: 14, 15, and 16, respectively, and the amino acid sequences of CDRs 1 to 3 of VL of the antibody contain the amino acid sequences represented by SEQ ID NOS: 17, 18, and 19, respectively;

(2b) an antibody which contains an amino acid sequence, in which one to three amino acid residues are deleted, substituted, added, or inserted in at least any one of the amino acid sequences of CDRs 1 to 3 of VH and CDRs 1 to 3 of VL of the antibody (2a), and has an antigen-binding activity equivalent to that of the antibody (2a); and (2c) an antibody, in which the amino acid sequences of CDRs 1 to 3 of VH of the antibody contain amino acid sequences having 80% or more homology with the amino acid sequences represented by SEQ ID NOS: 14, 15, and 16, respectively, and the amino acid sequences of CDRs 1 to 3 of VL of the antibody contain amino acid sequences having 80% or more homology with the amino acid sequences represented by SEQ ID NOS: 17, 18, and 19, respectively, and which has an antigen-binding activity equivalent to that of the antibody (2a).

8. The immunological measurement method according to the above 7, which is an enzyme immunoassay method or an immunochromatographic analysis method.

9. An immunological measurement device for detecting VZV, containing the antibody or the antibody fragment thereof according to any one of claims 1 to 6, wherein the immunological measurement device comprises a sample addition part, a labeling substance retaining part, a chromatographic medium part having a detection part, and an absorption part, and wherein the labeling substance retaining part and the detection part are the following (i) or (ii):

(i) the labeling substance retaining part contains any one of the antibodies (1a) to (1c) or an antibody fragment thereof, and the detection part contains any one of the antibodies (2a) to (2c) or an antibody fragment thereof; or (ii) the labeling substance retaining part contains any one of the antibodies (2a) to (2c) or an antibody fragment thereof, and the detection part contains any one of the antibodies (1a) to (1c) or an antibody fragment thereof.

10. The immunological measurement device according to the above 9, wherein a sample to be added to the sample addition part is a blister's fluid containing varicella-zoster virus.

11. An immunological measurement method, which is a method for detecting VZV in a specimen using the immunological measurement device according to the above 9 or 10, including the following steps (1) to (4):

(1) a step of adding a specimen-containing liquid obtained by diluting a specimen with a specimen diluent to the sample addition part;

(2) a step of allowing the antibody or the antibody fragment thereof retained in the labeling substance retaining part to recognize varicella-zoster virus;

(3) a step of developing the specimen and the antibody or the antibody fragment thereof in the chromatographic medium part as a mobile phase; and (4) a step of detecting varicella-zoster virus in the developed mobile phase by the antibody or the antibody fragment thereof contained in the detection part.

12. A nucleic acid, containing a base sequence encoding the antibody or the antibody fragment thereof according to any one of the above 1 to 6.

13. A transformed cell, including a vector containing the nucleic acid according to the above 12.

14. A method for producing the antibody or the antibody fragment thereof according to any one of the above 1 to 6, including culturing the transformed cell according to the above 13 and collecting the antibody or the antibody fragment thereof according to any one of the above 1 to 6 from a culture solution.

Aspects of certain non-limiting embodiments of the present disclosure address the features discussed above and/or other features not described above. However, aspects of the non-limiting embodiments are not required to address the above features, and aspects of the non-limiting embodiments of the present disclosure may not address features described above.

According to an aspect of the present disclosure, there is provided an antibody or an antibody fragment thereof which binds to glycoprotein E (gE) of varicella-zoster virus (VZV), and an immunological measurement method and an immunological measurement device using the antibody or the antibody fragment thereof. By using the antibody or the antibody fragment thereof of the present invention, VZV can be specifically detected rapidly and simply. That is, the diagnosis of varicella or zoster can be carried out more reliably and rapidly.

BRIEF DESCRIPTION OF DRAWINGS

Exemplary embodiment(s) of the present invention will be described in detail based on the following figures, wherein:

FIG. 1 is a cross-sectional view for illustrating a structure of an immunological measurement device of an exemplary embodiment of the present invention;

FIG. 2 is a schematic view showing the positions of respective peptide fragments in the full-length amino acid sequence of VZVgE; and FIG. 3 is a graph showing the results of an epitope analysis by a competitive inhibition test.

DESCRIPTION OF EMBODIMENTS

Hereinafter, the present invention will be described in detail, however, the invention is by no means limited to the following embodiments, and can be carried out by making appropriate changes within the scope of the object of the invention.

The value of homology in the present invention may be a value calculated using a homology search program known to those skilled in the art unless otherwise particularly specified, however, with respect to a base sequence, a value calculated using a default parameter in BLAST [J. Mol. Biol., 215, 403 (1990)], and the like are exemplified, and with respect to an amino acid sequence, a value calculated using a default parameter in BLAST2 [Nucleic Acids Res., 25, 3389 (1997), Genome Res., 7, 649 (1997), http://www.ncbi.nlm.nih.gov/Education/BLASTinfo/information3.html], and the like are exemplified.

As for the default parameters, G (Cost to open gap) is 5 in the case of a base sequence and 11 in the case of an amino acid sequence, -E (Cost to extend gap) is 2 in the case of a base sequence and 1 in the case of an amino acid sequence, -q (Penalty for nucleotide mismatch) is -3, -r (reward for nucleotide match) is 1, -e (expect value) is 10, -W (wordsize) is 11 residues in the case of a base sequence and 3 residues in the case of an amino acid sequence, -y [Dropoff (X) for blast extensions in bits] is 20 in the case of blastn and 7 in the case of programs other than blastn, -X (X dropoff value for gapped alignment in bits) is 15, and -Z (final X dropoff value for gapped alignment in bits) is 50 in the case of blastn and 25 in the case of programs other than blastn (http://www.ncbi.nlm.nih.gov/blast/html/blastcgihelp.html).

<VZVgE>

VZV belongs to the α-herpesvirinae and is a pathogenic mediator of varicella and zoster. Varicella-zoster virus glycoprotein E (VZVgE) which is one of the glycoproteins of this VZV is composed of 623 amino acids represented by SEQ ID NO: 1, and is constituted by an extracellular domain corresponding to the amino acid sequence at positions 1 to 544, a transmembrane domain (TM) corresponding to the amino acid sequence at positions 545 to 562, and a cytoplasmic tail corresponding to the amino acid sequence at positions 563 to 623 (Jurie K. et al., Journal of Virology, January 1997, pp. 110-119).

In the present invention, as VZVgE, a polypeptide which is composed of an amino acid sequence in which one or more amino acids are deleted, substituted, or added in the amino acid sequence represented by SEQ ID NO: 1 and has the function of VZVgE, a polypeptide which is composed of an amino acid sequence having 60% or more, preferably 80% or more, more preferably 90% or more, and most preferably 95% or more homology with the amino acid sequence represented by SEQ ID NO: 1 and has the function of VZVgE, or the like is exemplified.

The polypeptide which has an amino acid sequence in which one or more amino acids are deleted, substituted, or added in the amino acid sequence represented by SEQ ID NO: 1 can be obtained by, for example, introducing a site-specific mutation into a DNA encoding a polypeptide containing the amino acid sequence of SEQ ID NO: 1 using a site-specific mutagenesis method [Molecular Cloning, A Laboratory Manual, Second Edition, Cold Spring Harbor Laboratory Press (1989), Current Protocols in Molecular Biology, John Wiley & Sons (1987-1997), Nucleic acids Research, 10, 6487 (1982), Proc. Natl. Acad. Sci. USA, 79, 6409 (1982), Gene, 34, 315 (1985), Nucleic Acids Research, 13, 4431 (1985), Proc. Natl. Acad. Sci. USA, 82, 488 (1985)] or the like.

The number of amino acids to be deleted, substituted, or added is not particularly limited, but is preferably one to several tens, for example, 1 to 20, and more preferably one to several, for example, 1 to 5 amino acids.

<Antibody and Method for Producing Antibody>

The antibody or the antibody fragment thereof of the present invention specifically recognizes the amino acid sequence at positions 48 to 88 (SEQ ID NO: 3) in the amino acid sequence (SEQ ID NO: 1) of VZVgE. As one aspect of the antibody or the antibody fragment thereof of the present invention, an antibody which specifically recognizes the amino acid sequence represented by SEQ ID NO: 3, and does not specifically recognize the amino acid sequence at positions 48 to 67 (SEQ ID NO: 4), the amino acid sequence at positions 54 to 72 (SEQ ID NO: 5), the amino acid sequence at positions 62 to 81 (SEQ ID NO: 6), and the amino acid sequence at positions 69 to 88 (SEQ ID NO: 7) in the amino acid sequence represented by SEQ ID NO: 1 is exemplified. The reason why the antibody exhibits such reactivity is considered to be because the antibody recognizes a conformation composed of the amino acid sequence represented by SEQ ID NO: 3 and binds thereto.

Here, in this specification, the word "recognizes" in the phrase "an antibody recognizes a certain specific amino acid sequence" means that the antibody binds to the specific amino acid sequence with higher affinity than to the other amino acid sequences.

As described above, VZVgE has an about 50% amino acid sequence homology with the gE of the other α-herpesviruses. The antibody of the present invention recognizes the amino acid sequence at positions 48 to 88 in the amino acid sequence of VZVgE, and therefore can specifically detect VZV without crossreaction with the other α-herpesviruses with a high homology.

Further, as described later, for example, by including the antibody which recognizes the amino acid sequence at positions 48 to 88 in the amino acid sequence of VZVgE in a labeling substance retaining part and a detection part of an immunological measurement device including the labeling substance retaining part and the detection part, VZV can be efficiently detected with high accuracy.

As the antibody of the present invention, an antibody selected from the following (1a) to (1c), (2a) to (2c), (d), and (e) is exemplified.

(1a) an antibody in which the amino acid sequences of CDRs 1 to 3 of VH contain the amino acid sequences represented by SEQ ID NOS: 8, 9, and 10, respectively, and the amino acid sequences of CDRs 1 to 3 of VL contain the amino acid sequences represented by SEQ ID NOS: 11, 12, and 13, respectively.

(1b) an antibody which contains an amino acid sequence, in which one to three amino acid residues are deleted, substituted, added, or inserted in at least any one of the amino acid sequences of CDRs 1 to 3 of VH and CDRs 1 to 3 of VL of the antibody (1a), and has an antigen-binding activity equivalent to that of the antibody (1a).

(1c) an antibody, in which the amino acid sequences of CDRs 1 to 3 of VH of the antibody contain amino acid sequences having 80% or more homology with the amino acid sequences represented by SEQ ID NOS: 8, 9, and 10, respectively, and the amino acid sequences of CDRs 1 to 3 of VL of the antibody contain amino acid sequences having 80% or more homology with the amino acid sequences represented by SEQ ID NOS: 11, 12, and 13, respectively, and which has an antigen-binding activity equivalent to that of the antibody (1a).

(2a) an antibody in which the amino acid sequences of CDRs 1 to 3 of VH of the antibody contain the amino acid sequences represented by SEQ ID NOS: 14, 15, and 16, respectively, and the amino acid sequences of CDRs 1 to 3 of VL of the antibody contain the amino acid sequences represented by SEQ ID NOS: 17, 18, and 19, respectively.

(2b) an antibody which contains an amino acid sequence, in which one to three amino acid residues are deleted, substituted, added, or inserted in at least any one of the amino acid sequences of CDRs 1 to 3 of VH and CDRs 1 to 3 of VL of the antibody (2a), and has an antigen-binding activity equivalent to that of the antibody (2a).

(2c) an antibody, in which the amino acid sequences of CDRs 1 to 3 of VH of the antibody contain amino acid sequences having 80% or more homology with the amino acid sequences represented by SEQ ID NOS: 14, 15, and 16, respectively, and the amino acid sequences of CDRs 1 to 3 of VL of the antibody contain amino acid sequences having 80% or more homology with the amino acid sequences represented by SEQ ID NOS: 17, 18, and 19, respectively, and which has an antigen-binding activity equivalent to that of the antibody (2a).

(d) an antibody which competes for binding to VZVgE with at least one of the antibodies described in the above (1a) to (1c) and (2a) to (2c).

(e) an antibody which binds to the same epitope as an epitope to which any one of the antibodies described in the above (1a) to (1c) and (2a) to (2c) binds.

As the antibody of the present invention, an antibody which contains the amino acid sequences of CDRs 1 to 3 of VH and CDRs 1 to 3 of VL of an antibody showing 90% or more homology with the amino acid sequences of CDRs 1 to 3 of VH and CDRs 1 to 3 of VL, respectively, of any one of the antibodies described in the above (1a) to (1c), (2a) to (2c), (d), and (e) is included. As the 90% or more homology, specifically, 91%, 92%, 93%, 94%, 95%, 96%, 97%, 98%, and 99% homology, and the like are exemplified.

As one aspect of the antigen-binding activity, an activity of specifically binding to the amino acid sequence at positions 48 to 88 in the amino acid sequence represented by SEQ ID NO: 1 is exemplified. As one aspect of the antigen-binding activity, for example, an activity of specifically binding to the amino acid sequence at positions 48 to 88 in the amino acid sequence represented by SEQ ID NO: 1, but not recognizing the amino acid sequences represented by SEQ ID NOS: 4 to 7, respectively, is exemplified.

The condition that the antibody or the antibody fragment thereof of the present invention "specifically binds to the amino acid sequence at positions 48 to 88 in the amino acid sequence represented by SEQ ID NO: 1" specifically means, for example, that when a peptide composed of the amino acid sequence represented by SEQ ID NO: 1 and a peptide composed of the amino acid sequence represented by SEQ ID NO: 3 are subjected to a competitive inhibition test by an ELISA method (competitive inhibition ELISA test) described later in Example, a reaction of an antibody with the peptide composed of the amino acid sequence represented by SEQ ID NO: 1 is competitively inhibited by the presence of the peptide composed of the amino acid sequence represented by SEQ ID NO: 3.

From the viewpoint of enhancing the detection sensitivity and specificity, with respect to the reaction of the antibody with the peptide composed of the amino acid sequence represented by SEQ ID NO: 1, when the absorbance in the case where the peptide composed of the amino acid sequence represented by SEQ ID NO: 3 is not added (control) is assumed to be 100%, the absorbance in the competitive inhibition ELISA test is preferably 50% or less, more preferably 25% or less, further more preferably 12.5% or less, particularly preferably 10% or less, and most preferably 5% or less.

The antibody or the antibody fragment thereof of the present invention preferably does not recognize the amino acid sequences represented by SEQ ID NOS: 4 to 7, respectively, in the amino acid sequence represented by SEQ ID NO: 1. According to this, the specificity and detection sensitivity can be further improved. The condition that the antibody in the present invention "does not recognize the amino acid sequences" includes that the antibody substantially does not show reactivity with a peptide composed of the amino acid sequences represented by SEQ ID NOS: 4 to 7, respectively. Specifically, for example, in the below-mentioned competitive inhibition ELISA test in Example, the absorbance with respect to that of the control is preferably −25% or less, more preferably −20% or less, further more preferably −15% or less, and particularly preferably −10% or less.

The above antibody (d) of the present invention refers to, when an antibody described in at least any one of the above (1a) to (1c) and (2a) to (2c) is defined as a first antibody, a second antibody that inhibits binding of the first antibody to VZVgE. The above antibody (e) of the present invention refers to, when an antibody described in any one of the above (1a) to (1c) and (2a) to (2c) is defined as a first antibody and an epitope to which the first antibody binds is defined as a first epitope, a second antibody that binds to the first epitope.

Further, as the antibody of the present invention, specifically, the following antibody (I) or (II) is also exemplified.

(I) an antibody in which the amino acid sequence of VH is the amino acid sequence represented by SEQ ID NO: 20 and the amino acid sequence of VL is the amino acid sequence represented by SEQ ID NO: 21

(II) an antibody in which the amino acid sequence of VH is the amino acid sequence represented by SEQ ID NO: 22 and the amino acid sequence of VL is the amino acid sequence represented by SEQ ID NO: 23

As the antibody of the present invention, an antibody which contains the amino acid sequences of VH and VL of an antibody showing 90% or more homology with the amino acid sequences of VH and VL, respectively, of the above antibody (I) or (II) is included. As the 90% or more homology, specifically, 91%, 92%, 93%, 94%, 95%, 96%, 97%, 98%, and 99% homology, and the like are exemplified.

Further, as one aspect of the antibodies described in the above (I) and (II), Antibody 9 and Antibody 18, respectively, are exemplified.

As the antibody of the present invention, any antibody of a polyclonal antibody, a monoclonal antibody, and an oligoclonal antibody is included. The polyclonal antibody refers to a collection of antibody molecules secreted by antibody-producing cells of different clones. The monoclonal antibody is an antibody secreted by an antibody-producing cell of a single clone, and refers to an antibody, which recognizes only a single epitope (also referred to as an antigenic determinant), and in which an amino acid sequence (primary sequence) constituting the monoclonal antibody is uniform. The oligoclonal antibody refers to a collection of antibody molecules in which a plurality of different monoclonal antibodies are mixed.

As the monoclonal antibody in the present invention, an antibody produced by a hybridoma, or a genetically recombinant antibody produced by a transformant transformed with an expression vector containing an antibody gene can be exemplified.

As the epitope, a single amino acid sequence, a conformation composed of an amino acid sequence, an amino acid sequence modified by post-translational modification, a conformation composed of the amino acid sequence, each of which the monoclonal antibody recognizes and binds to, and the like are exemplified.

As the amino acid sequence modified by post-translational modification, an amino acid sequence to which an O-linked glycan in which a glycan is attached to Tyr and Ser each having an OH substituent, an N-linked glycan in which a glycan is attached to Gln and Asn each having an $NH_2$ substituent, and a sulfate group in which a sulfuric acid molecule is attached to Tyr having an OH substituent, or the like is attached is exemplified.

It can be confirmed that the antibody of the present invention binds to VZVgE by measuring the binding activity of the antibody of the present invention to a cell expressing VZVgE using ELISA, flow cytometry, a surface plasmon resonance method, or the like. Further, it can also be confirmed using known immunological detection methods [Monoclonal Antibodies-Principles and practice, Third edition, Academic Press (1996), Antibodies-A Laboratory Manual, Cold Spring Harbor Laboratory (1988), Manual for monoclonal antibody experiments, Kodansha scientific books (1987)], and the like in combination.

As the antibody of the present invention, in particular, genetically recombinant antibodies such as a recombinant mouse antibody, a recombinant rat antibody, a recombinant rabbit antibody, a human chimeric antibody (hereinafter, also simply abbreviated as a chimeric antibody), a humanized antibody (also referred to as a human complementarity-determining region CDR-grafted antibody), and a human antibody, each of which is produced by genetic engineering are also included.

The chimeric antibody means an antibody composed of VH and VL of an antibody of an animal other than a human (non-human animal) and CH and CL of a human antibody. As the non-human animal, any animal such as a mouse, a rat, a hamster, or a rabbit can be used as long as it can produce a hybridoma.

The hybridoma refers to a cell which is obtained by cell fusion of a B cell obtained by immunizing a non-human animal with an antigen and a myeloma cell derived from a mouse or the like and which produces a monoclonal antibody having a desired antigen specificity. Therefore, a variable region constituting an antibody that the hybridoma produces is composed of an amino acid sequence of a non-human animal antibody.

The human chimeric antibody can be produced by obtaining cDNAs encoding VH and VL of a monoclonal antibody from a hybridoma derived from a non-human animal cell which produces the monoclonal antibody, inserting each of the cDNAs into an expression vector for animal cells having DNAs encoding CH and CL of a human antibody, thereby constructing a human chimeric antibody expression vector, and then introducing the vector into an animal cell to express the antibody.

The humanized antibody refers to an antibody in which the amino acid sequences of CDRs of VH and VL of a non-human animal antibody are grafted into the corresponding CDRs of VH and VL of a human antibody. A region other than CDRs of VH and VL is called a framework region (hereinafter referred to as FR).

The humanized antibody can be produced by constructing a cDNA encoding the amino acid sequence of VH composed of the amino acid sequence of CDR of VH of a non-human animal antibody and the amino acid sequence of FR of VH of an arbitrary human antibody, and a cDNA encoding the amino acid sequence of VL composed of the amino acid sequence of CDR of VL of a non-human animal antibody and the amino acid sequence of FR of VL of an arbitrary human antibody, inserting each of the cDNAs into an expression vector for animal cells having DNAs encoding CH and CL of a human antibody, thereby constructing a humanized antibody expression vector, and then introducing the vector into an animal cell to express the antibody.

The human antibody originally refers to an antibody that naturally exists in the human body, but also includes antibodies obtained from a human antibody phage library and a human antibody-producing transgenic animal produced due to recent advancement of genetic engineering, cell engineering, and developmental engineering techniques, and the like.

The human antibody can be obtained by immunizing a mouse having a human immunoglobulin gene (Tomizuka K. et al., Proc. Natl. Acad. Sci. USA. 97, 722-7, 2000) with a desired antigen. In addition, the human antibody can be obtained without performing immunization by selecting a human antibody having a desired binding activity using a phage display library obtained by amplifying an antibody gene from human-derived B cells (Winter G. et al., Annu. Rev. Immunol. 12: 433-55, 1994). Further, the human antibody can be obtained by producing cells which produce a human antibody having a desired binding activity by immortalizing human B cells using EB virus (Rosen A. et al., Nature, 267, 52-54, 1977).

As for the antibody existing in the human body, for example, lymphocytes isolated from human peripheral blood are infected with EB virus or the like so as to immortalize the lymphocytes, followed by cloning, whereby a lymphocyte that produces the antibody can be obtained, and the antibody can be purified from a culture obtained by culturing the lymphocyte.

The human antibody phage library is a library of phages in which an antibody fragment such as Fab or scFv is expressed on the surface thereof by inserting an antibody gene prepared from a human B cell into a phage gene. It is possible to collect a phage that expresses an antibody fragment having a desired antigen-binding activity from the library using a binding activity to a substrate onto which an antigen is immobilized as an index. The antibody fragment can also be further converted into a human antibody molecule composed of two complete H chains and two complete L chains using a genetic engineering technique.

The human antibody-producing transgenic animal refers to an animal in which a human antibody gene is incorporated into the chromosome of a host animal. Specifically, a human antibody-producing transgenic animal can be produced by introducing a human antibody gene into a mouse ES cell, implanting the ES cell into an early embryo of another mouse and then allowing the embryo to develop into an animal. As for a method for producing a human antibody from the human antibody-producing transgenic animal, a human antibody-producing hybridoma is obtained by a general hybridoma production method to be performed using a mammal other than a human, followed by culturing, whereby a human antibody can be produced and accumulated in the culture.

The amino acid sequences of VH and VL of the antibody of the present invention may be any of the amino acid sequences of VH and VL of a human antibody, the amino acid sequences of VH and VL of a non-human animal antibody, and the amino acid sequences of VH and VL of a humanized antibody in which CDR of a non-human animal antibody is grafted into a framework of an arbitrary human antibody.

The amino acid sequence of CL of the antibody of the present invention may be either of the amino acid sequence of a human antibody and the amino acid sequence of a non-human animal antibody, but is preferably Cκ or Cλ of the amino acid sequence of a human antibody.

The CH of the antibody of the present invention may be any as long as it belongs to immunoglobulin, but preferably, any of subclass belonging to IgG class, γ1 (IgG1), γ2 (IgG2), γ3 (IgG3), and γ4 (IgG4) can be used.

As the antibody of the present invention, an Fc fusion protein in which Fc and an antibody fragment are bound, an Fc fusion protein in which Fc and a naturally existing ligand or receptor are bound (also, referred to as immunoadhesin), an Fc fusion protein in which a plurality of Fc regions are fused, and the like are also included in the present invention. In addition, in order to stabilize the antibody and to control the blood half-life, an Fc region with a modified amino acid residue can also be used in the antibody of the present invention.

The antibody or the antibody fragment thereof of the present invention includes an antibody containing any amino acid residue subjected to post-translational modification. Examples of the post-translational modification include deletion of a lysine residue at the C-terminus of an H chain [lysine clipping] or conversion of a glutamine residue at the N-terminus of a polypeptide to pyroglutamine (pyroGlu) [Beck et al, Analytical Chemistry, 85, 715-736 (2013)], and the like.

In the present invention, the antibody fragment is an antibody fragment which binds to VZVgE and has an antigen-binding activity. Examples of the antibody fragment in the present invention include Fab, Fab', F(ab')2, scFv, a diabody, dsFv, a peptide including a plurality of CDRs, and the like. Fab is an antibody fragment, which has a molecular weight of about 50,000 and has an antigen-binding activity, and in which about a half of an H chain at the N-terminal side and the entire L chain are bound through a disulfide bond (S—S bond) among the fragments obtained by treating an IgG antibody with a protease papain (cleaved at an amino acid residue at position 224 in the H chain).

$F(ab')_2$ is an antibody fragment, which has a molecular weight of about 100,000 and has an antigen-binding activity, and is slightly larger than a molecule obtained by binding Fabs through an S—S bond in the hinge region among the fragments obtained by treating IgG with a protease pepsin (cleaved at an amino acid residue at position 234 in the H chain). Fab' is an antibody fragment, which has a molecular weight of about 50,000 and has an antigen-binding activity, and in which an S—S bond in the hinge region of the above $F(ab')_2$ is cleaved.

scFv is a VH-P-VL or VL-P-VH polypeptide in which one VH and one VL are linked using an appropriate peptide linker (P) such as a linker peptide obtained by connecting an arbitrary number of linkers (G4S) composed of four Gly residues and one Ser residue, and is an antibody fragment having an antigen-binding activity.

The diabody is an antibody fragment in which scFvs having the same or different antigen-binding specificities form a dimer, and is an antibody fragment having a divalent antigen-binding activity to the same antigen or antigen-binding activities specific for different antigens.

The dsFv is an antibody fragment, which is obtained by binding polypeptides in which one amino acid residue in each of VH and VL is substituted with a cysteine residue through an S—S bond between the cysteine residues.

The peptide including CDR is configured to include at least one or more regions of CDRs of VH or VL. In a peptide including a plurality of CDRs, the CDRs can be bound directly or through an appropriate peptide linker. Production can be carried out by constructing DNAs encoding CDRs of VH and VL of a modified antibody of the present invention, inserting the DNAs into an expression vector for a prokaryote or an expression vector for a eukaryote, and then introducing the expression vector into a prokaryote or a eukaryote to express the peptide. In addition, the peptide including CDR can also be produced by a chemical synthesis method such as an Fmoc method or a tBoc method.

The method for producing the antibody or the antibody fragment thereof is not particularly limited, and the antibody or the antibody fragment thereof can be produced, for example, by generic engineering based on the above-mentioned amino acid sequence information. Specifically, for example, the production can be carried out as follows. The present invention is not limited to this example.

First, a vector containing a nucleic acid sequence encoding the amino acid sequence of any of the above-mentioned respective regions, the above-mentioned heavy chain, and/or light chain in the antibody is introduced into a host, whereby a transformant is obtained. Then, the transformant is cultured, and a fraction containing the antibody which binds to VZVgE is collected, and the antibody is isolated or purified from the obtained collected fraction.

Examples of the vector include a vector containing a nucleic acid sequence encoding a heavy chain variable region, a vector containing a nucleic acid sequence encoding a light chain variable region, a vector containing a nucleic acid sequence encoding a heavy chain, a vector containing a nucleic acid sequence encoding a light chain, and the like.

As a culture method for the transformant is not particularly limited, and can be appropriately determined according to the type of the host. The fraction containing the antibody can be collected as a liquid fraction, for example, by homogenizing the cultured transformant. The isolation or purification of the antibody is not particularly limited, and a known method can be adopted.

The host is not particularly limited, and may be any as long as a vector can be introduced, and the nucleic acid sequence in the vector can be expressed. Examples of the host include mammalian cells such as HEK cells, CHO cells, COS cells, NSO cells, and SP2/0 cells, and the like. The method for introducing the vector into the host is not particularly limited, and a known method can be adopted.

Examples of the antibody-producing animal species include a human, a mouse, a rat, a rabbit, a goat, a horse, and the like. The immunoglobulin may be any of IgG, IgM, IgA, IgE, and IgD.

In one embodiment, a VZVgE peptide as an immunogen can be produced by a known general production method. That is, a gE protein extracted and purified from VZV containing the amino acid sequence of SEQ ID NO: 1, or a gE protein obtained by expressing a cloned gE protein gene in a host such as *E. coli* through genetic engineering followed by extraction and purification, or further a polypeptide constituting a portion of the gE protein can be used as the immunogen.

The monoclonal antibody is obtained according to a conventional method as follows. The spleen cells and myeloma cells of a mouse immunized with the above-mentioned immunogen are fused, and a hybridoma which produces a target antibody is selected, and a monoclonal antibody produced from this hybridoma is obtained [see, for example, the method of Kohler and Milstein [Nature, 256 (1975), 495-497]. The polyclonal antibody is obtained by separating a target antibody from an antiserum obtained by immunizing an antibody-producing animal (for example, a human, a mouse, a rat, a rabbit, a goat, a horse, etc.) with the above-mentioned immunogen according to a conventional method.

The screening of the hybridoma clone which produces a monoclonal antibody can be carried out by culturing the hybridoma in, for example, a microtiter plate, and the reactivity with the immunogen in a culture supernatant in a well in which proliferation is observed is measured by, for example, an enzyme immunoassay method such as ELISA.

This hybridoma is cultured using a culture medium (for example, DMEM containing 10% fetal bovine serum), and the centrifugal supernatant of the culture solution can be used as a monoclonal antibody solution. Further, this hybridoma is injected into the abdominal cavity of an animal from which this hybridoma is derived so as to allow the animal to produce an ascites, and the obtained ascites can be used as a monoclonal antibody solution. The monoclonal antibody is preferably isolated and/or purified.

Among the antibodies which recognize VZVgE, an antibody which recognizes a specific region of the amino acid sequence of VZVgE can be obtained by, for example, selecting a hybridoma which produces an antibody that shows a higher reactivity with the specific region of the amino acid sequence of VZVgE from the hybridomas which produce an antibody that recognizes VZVgE by Western blotting or the like using a fragment of a protein corresponding to the specific region of the amino acid sequence of VZVgE.

The amino acid sequence of the anti-VZVgE antibody can be obtained according to a conventional method. For example, mRNA is extracted with phenol/chloroform from the cultured hybridoma, and thereafter, the mRNA is converted to cDNA, and PCR is performed using primers designed complementary to the constant region or the FR portion of the antibody, and then, the gene sequence of the amplified gene product can be obtained by a Sanger sequencing method or the like [see, for example, Journal of Immunological Methods 233, 167-177 (2000)]. The obtained gene sequence is converted to an amino acid sequence, and the obtained amino acid sequence is analyzed by IgBLAST, BLAST, or the like, whereby the amino acid sequence of the antibody can be obtained.

Specifically, as shown in Examples, for example, the antibody which specifically recognizes the amino acid sequence at positions 48 to 88 in the amino acid sequence of VZVgE is obtained by performing screening as described below. For example, as described later in Examples, a hybridoma which produces an antibody that shows a higher reactivity with the amino acid sequence at positions 48 to 88 in the amino acid sequence of VZVgE can be selected from the hybridomas which produce the antibody that recognizes VZVgE using a protein fragment composed of the amino acid sequence at positions 48 to 88 in the amino acid sequence of VZVgE.

Hereinabove, the method for producing the antibody to be used in the present invention has been described, and will be specifically described in detail in Examples.

<Immunological Measurement Method>

VZV can be diagnosed by detecting or measuring VZVgE using the antibody or the antibody fragment thereof of the present invention. The diagnosis of VZV can be carried out, for example, by detecting or measuring VZVgE present in the body of a patient using an immunological method. Further, the diagnosis can be carried out by detecting VZVgE expressed in a cell in the body of a patient using an immunological measurement method.

The immunological measurement method is a method for detecting or measuring the amount of an antibody or the amount of an antigen using a labeled antigen or antibody. Examples of the immunological measurement method include an immunochromatographic analysis method, a radioactive material labeled immune antibody method, an enzyme immunoassay method, a fluorescence immunoassay method, a luminescence immunoassay method, a Western blotting method, a physicochemical method, and the like. Among these, an immunochromatographic analysis method and an enzyme immunoassay method are preferred.

<<Immunological Measurement Device>>

One embodiment of an immunological measurement device to be used in the immunological measurement method will be described. The immunological measurement device of the present invention contains the antibody or the antibody fragment thereof of the present invention in a labeling substance retaining part and a detection part. It is preferred that the immunological measurement device of the present invention contains any one of the above-mentioned antibodies (1a) to (1c) or an antibody fragment thereof in one of the labeling substance retaining part and the detection part, and contains any one of the above-mentioned antibodies (2a) to (2c) or an antibody fragment thereof in the other.

That is, in one embodiment of the immunological measurement device of the present invention, it is preferred that the labeling substance retaining part and the detection part are the following (i) or (ii).

(i) the labeling substance retaining part contains any one of the following antibodies (1a) to (1c) or an antibody fragment thereof, and the detection part contains any one of the following antibodies (2a) to (2c) or an antibody fragment thereof.

(ii) the labeling substance retaining part contains any one of the following antibodies (2a) to (2c) or an antibody fragment thereof, and the detection part contains any one of the following antibodies (1a) to (1c) or an antibody fragment thereof.

(1a) an antibody in which the amino acid sequences of CDRs 1 to 3 of VH contain the amino acid sequences represented by SEQ ID NOS: 8, 9, and 10, respectively, and the amino acid sequences of CDRs 1 to 3 of VL contain the amino acid sequences represented by SEQ ID NOS: 11, 12, and 13, respectively.

(1b) an antibody which contains an amino acid sequence, in which one to three amino acid residues are deleted, substituted, added, or inserted in at least any one of the amino acid sequences of CDRs 1 to 3 of VH and CDRs 1 to 3 of VL of the antibody (1a), and has an antigen-binding activity equivalent to that of the antibody (1a).

(1c) an antibody, in which the amino acid sequences of CDRs 1 to 3 of VH of the antibody contain amino acid sequences having 80% or more homology with the amino acid sequences represented by SEQ ID NOS: 8, 9, and 10, respectively, and the amino acid sequences of homology with the amino acid sequences represented by SEQ ID NOS: 11, 12, and 13, respectively, and which has an antigen-binding activity equivalent to that of the antibody (1a).

(2a) an antibody in which the amino acid sequences of CDRs 1 to 3 of VH of the antibody contain the amino acid sequences represented by SEQ ID NOS: 14, 15, and 16, respectively, and the amino acid sequences of CDRs 1 to 3 of VL of the antibody contain the amino acid sequences represented by SEQ ID NOS: 17, 18, and 19, respectively.

(2b) an antibody which contains an amino acid sequence, in which one to three amino acid residues are deleted, substituted, added, or inserted in at least any one of the amino acid sequences of CDRs 1 to 3 of VH and CDRs 1 to 3 of VL of the antibody (2a), and has an antigen-binding activity equivalent to that of the antibody (2a).

(2c) an antibody, in which the amino acid sequences of CDRs 1 to 3 of VH of the antibody contain amino acid sequences having 80% or more homology with the amino acid sequences represented by SEQ ID NOS: 14, 15, and 16, respectively, and the amino acid sequences of CDRs 1 to 3 of VL of the antibody contain amino acid sequences having 80% or more homology with the amino acid sequences represented by SEQ ID NOS: 17, 18, and 19, respectively, and which has an antigen-binding activity equivalent to that of the antibody (2a).

The reason why it is preferred that any one of the above-mentioned antibodies (1a) to (1c) or an antibody fragment thereof is contained in one of the labeling substance retaining part and the detection part, and any one of the above-mentioned antibodies (2a) to (2c) or an antibody fragment thereof is contained in the other is that a region of VZVgE recognized by the antibody (hereinafter also referred to as "first antibody") or an antibody fragment thereof supported on the labeling substance retaining part and a region of VZVgE recognized by an antibody (hereinafter also referred to as "second antibody") or an antibody fragment thereof supported on the detection part are different from each other, and therefore, a sandwich structure as shown below is formed without masking the epitope by antibody binding, or without undergoing an interaction such as an effect of the conformational change of an antigen, so that the detection sensitivity is improved. That is, first, the antibody (first antibody) or an antibody fragment thereof supported on the labeling substance retaining part binds to a portion of VZVgE. Subsequently, the antibody (second antibody) or an antibody fragment thereof fixed on the detection part binds to another portion which is different from the portion to which the first antibody or an antibody fragment thereof binds, whereby a sandwich structure is formed such that VZVgE is interposed between the antibodies or the antibody fragments thereof, and thus, VZV is detected.

Next, one embodiment of the immunological measurement device of the present invention will be described with reference to the drawing. In this specification, the "fixing" means that the antibody or an antibody fragment thereof is placed on a carrier such as a membrane so that the antibody or an antibody fragment thereof does not move, and the "supporting" or "retaining" means that the antibody or an antibody fragment thereof is movably placed in a carrier such as a membrane or on the surface thereof.

According to one embodiment of the immunological measurement device of the present invention, as shown in FIG. 1, the device is constituted by a sample addition part (also referred to as "sample pad") (1), a labeling substance retaining part (also referred to as "conjugate pad") (2), a chromatographic medium part (3), a detection part (4), an absorption part (5), and a backing sheet (6).

The sample addition part (1) is a part where a specimen (sample) is added dropwise in the immunological measurement device. The sample addition part (1) can be constituted by a porous sheet having a property such that the specimen sample is rapidly absorbed, but the retaining power is weak and the specimen sample promptly migrates therein. Examples of the porous sheet include a cellulose filter paper, a glass fiber filter paper, polyurethane, polyacetate, cellulose acetate, nylon, a cotton cloth, and the like.

The labeling substance retaining part (2) contains the below-mentioned labeling substance (marker substance), and the labeling substance is supported on the labeling substance retaining part (2) as a labeling antibody in which the labeling substance and the antibody are bound to each other. The antibody (first antibody) or an antibody fragment thereof which binds to the labeling substance preferably includes any one of the above-mentioned antibodies (1a) to (1c) or an antibody fragment thereof, or any one of the above-mentioned antibodies (2a) to (2c) or an antibody fragment thereof as described above.

When the antibody (first antibody) or an antibody fragment thereof supported on the labeling substance retaining part (2) is any one of the above-mentioned antibodies (1a) to (1c) or an antibody fragment thereof, it is preferred that the antibody (second antibody) or an antibody fragment thereof to be contained in the below-mentioned detection part (4) is any one of the above-mentioned antibodies (2a) to (2c) or an antibody fragment thereof.

When the antibody (first antibody) or an antibody fragment thereof supported on the labeling substance retaining part (2) is any one of the above-mentioned antibodies (2a) to (2c) or an antibody fragment thereof, it is preferred that the antibody (second antibody) or an antibody fragment thereof to be contained in the below-mentioned detection part (4) is any one of the above-mentioned antibodies (1a) to (1c) or an antibody fragment thereof. When the specimen migrates in the labeling substance retaining part, the labeling antibody (first antibody) or an antibody fragment thereof and VZV in the specimen bind to each other. In the labeling substance retaining part (2), a glass fiber or cellulose membrane is generally used.

The content of the antibody (first antibody) or an antibody fragment thereof in the labeling substance retaining part is generally from 0.03 to 0.50 μg, preferably from 0.05 to 0.4 μg, and more preferably from 0.1 to 0.3 μg. Further, the content of the antibody (first antibody) or an antibody fragment thereof per unit area of the labeling substance retaining part is generally from 0.05 to 1.0 $\mu g/cm^2$, preferably from 0.1 to 0.8 $\mu g/cm^2$, and more preferably from 0.17 to 0.6 $\mu g/cm^2$.

In the labeling of a detection reagent in immunological measurement, an enzyme or the like is also generally used, however, it is preferred to use an insoluble carrier as the labeling substance since it is suitable for determining the presence of a detection target by visual observation. The labeled detection reagent can be prepared by sensitizing the antibody to the insoluble carrier. In this connection, a method for sensitizing the antibody to the insoluble carrier may be performed in accordance with a known method.

As the insoluble carrier to serve as the labeling substance, colloidal metal particles such as gold, silver, or platinum, colloidal metal oxide particles such as iron oxide, colloidal non-metal particles such as sulfur, latex particles composed of a synthetic polymer, or other insoluble carriers can be used. In particular, gold colloidal particles are preferred since detection is simple, aggregation is less likely to occur, and also nonspecific color development is less likely to occur. The average particle diameter of the gold colloidal particles is, for example, from 10 nm to 250 nm, and preferably from 35 nm to 120 nm. The average particle diameter can be obtained by randomly measuring the projected area circle equivalent diameters of 100 particles using a projected image taken by a transmission electron microscope (TEM, manufactured by JEOL Ltd., JEM-2010), and calculating the average of the projected area circle equivalent diameters. The amount of the gold colloidal particles contained in the labeling substance retaining part per unit area of the labeling substance retaining part is generally from 0.025 to 1.5 $\mu g/cm^2$, preferably from 0.05 to 1.5 $\mu g/cm^2$, more preferably from 0.1 to 1.0 $\mu g/cm^2$, and further more preferably from 0.2 to 0.6 $\mu g/cm^2$. This is because by setting the amount within the above range, the labeled particles are developed while being dispersed, and high sensitivity can be achieved without inhibiting the recognition site of the antibody.

The insoluble carrier is the labeling substance suitable for visually determining the presence of the detection target, and is preferably a colored substance in order to facilitate the determination by visual observation. The colloidal metal particles and the colloidal metal oxide particles exhibit a specific natural color per se according to the particle diameter, and the color can be utilized as a label.

The chromatographic medium part (3) is a developing part in a chromatograph. The chromatographic medium part (3) is an inactive membrane composed of a microporous material exhibiting a capillary phenomenon. From the viewpoint of having no reactivity with a detection reagent, a fixing reagent, a detection target, and the like to be used in the chromatograph and also from the viewpoint of enhancing the effect of the present invention, for example, a membrane made of nitrocellulose (hereinafter also referred to as "nitrocellulose membrane") or a membrane made of cellulose acetate (hereinafter also referred to as "cellulose acetate membrane") is preferred, and a nitrocellulose membrane is more preferred. In this connection, it is also possible to use a cellulose-based membrane, a nylon membrane, and a porous plastic fabric (polyethylene or polypropylene).

The nitrocellulose membrane may be any as long as it contains nitrocellulose as a main component, and a membrane which contains nitrocellulose as a main material such as a pure product or a nitrocellulose mixed product can be used.

It is also possible to further incorporate a substance which promotes a capillary phenomenon in the nitrocellulose membrane. As the substance, a substance which lowers the surface tension of the membrane surface to impart hydrophilicity is preferred. For example, a substance which has amphiphilicity, has no effect on the migration of the detection target, and does not affect the color development of the marker substance (for example, gold colloidal particles, or the like) such as a saccharide, an amino acid derivative, a fatty acid ester, any of a variety of synthetic surfactants, or an alcohol is preferred.

The nitrocellulose membrane is a porous material and exhibits a capillary phenomenon. The index of this capillary phenomenon can be confirmed by measuring a water absorption speed (water absorption time: capillary flow time). The water absorption speed affects the detection sensitivity and the test time.

The form and size of the chromatographic medium part (3) represented by a nitrocellulose membrane or a cellulose acetate membrane as described above are not particularly limited, and may be any as long as they are appropriate in terms of actual operation and observation of the reaction result.

Further, in order to make the operation simpler, it is preferred to provide a support made of a plastic or the like on the rear surface of the chromatographic medium part (3). The property of this support is not particularly limited, however, when the measurement result is observed by visual determination, the support preferably has a color which is not similar to the color brought about by the labeling substance, and is generally preferably colorless or white.

The detection part (4) is formed on the chromatographic medium part (3). Namely, an antibody which recognizes VZV is fixed at an arbitrary position on the chromatographic medium part (3). The fixing of the antibody can be carried out according to a conventional method.

The content of the antibody (second antibody) or an antibody fragment thereof in the detection part (4) is generally from 0.1 to 3.0 μg, preferably from 0.3 to 2.0 μg, and more preferably from 0.3 to 1.0 μg. Further, the content of the antibody (second antibody) or an antibody fragment thereof per unit area of the detection part (4) is generally from 0.04 to 1.0 $g/cm^2$, preferably from 0.125 to 0.8 $\mu g/cm^2$, and more preferably from 0.125 to 0.42 $\mu g/cm^2$.

Further, on the chromatographic medium part (3), in order to prevent the decrease in the analysis accuracy due to nonspecific adsorption, according to need, the chromatographic medium part (3) may be subjected to a blocking treatment by a known method. In general, in the blocking treatment, a protein such as bovine serum albumin, skim milk, casein, or gelatin is preferably used. After such a blocking treatment, according to need, for example, washing may be performed by using one surfactant such as Tween (registered trademark) 20, Triton (registered trademark) X-100, SDS, or the like, or two or more surfactants in combination.

In the detection part (4), an anti-IgG antibody application part on which an anti-IgG antibody is supported as a control other than the above-mentioned second antibody or an antibody fragment thereof may be provided. The part is configured such that the labeling substance of the labeling antibody which did not react with the antigen or the labeling substance of the labeling antibody which did not react with the second antibody or an antibody fragment thereof reacts with the anti-IgG antibody in this anti-IgG antibody application part and is fixed thereon, and therefore functions as a control which shows that development is carried out normally.

The absorption part (5) is provided for absorbing a liquid of the specimen, the developing solution, or the like having passed through the detection part (4) at an end of the chromatographic medium part (3). In the immunological measurement device of the present invention, the absorption part (5) can be composed of, for example, glass fiber. When the absorption part (5) is composed of glass fiber, the backward migration of the sample solution can be greatly reduced.

The backing sheet (6) is a base material. By applying an adhesive to one surface or sticking an adhesive tape to one surface, the surface has adhesiveness, and on the adhesive surface, part or all of the sample addition part (1), the labeling substance retaining part (2), the chromatographic medium part (3), the detection part (4), and the absorption part (5) are provided in close contact with the surface. The backing sheet (6) is not particularly limited as the base material as long as it becomes impermeable to a sample solution and also impermeable to moisture by the adhesive.

The immunological measurement device prepared as described above is generally subjected to a drying treatment before being made into a product. The drying temperature is, for example, from 20 to 50° C., and the drying time is from 0.5 to 1 hour.

<<Immunochromatographic Analysis Method>>

As one aspect of the immunological measurement method of the present invention, an immunochromatographic analysis method will be described. The immunochromatographic analysis method is a method for detecting VZV which is a detection target contained in a specimen using the above-mentioned immunological measurement device, and preferably includes the following steps (1) to (4).

(1) a step of adding a specimen-containing solution obtained by diluting a specimen with a specimen diluent to the sample addition part (2) a step of allowing an antibody or an antibody fragment thereof retained in the labeling substance retaining part to recognize varicella-zoster virus (3) a step of developing the specimen and the antibody or an antibody fragment thereof in the chromatographic medium part as a mobile phase (4) a step of detecting varicella-zoster virus in the developed mobile phase by an antibody or an antibody fragment thereof contained in the detection part Both the labeling substance retaining part and the detection part in the above-mentioned immunological measurement device used in the immunological measurement method of the present invention contain the antibody or the antibody fragment thereof of the present invention. As described above, in particular, in the immunological measurement device, the labeling substance retaining part and the detection part contain the antibody or the antibody fragment thereof of the present invention. It is preferred that in the immunological measurement device of the present invention, one of the labeling substance retaining part and the detection part contains any one of the above-mentioned antibodies (1a) to (1c) or an antibody fragment thereof, and the other one contains any one of the above-mentioned antibodies (2a) to (2c) or an antibody fragment thereof.

The respective steps will be described below.

(1) Step of Adding Specimen-Containing Solution Obtained by Diluting Specimen with Specimen Diluent to Sample Addition Part In the step (1), in the first place, a specimen-containing solution is preferably formed by appropriately preparing or diluting a specimen with a specimen diluent to such a concentration that the specimen migrates smoothly in the immunochromatographic medium without decreasing the measurement accuracy. As the specimen diluent, the above-mentioned specimen diluent can be used. In the second place, the specimen-containing solution is added dropwise onto the sample addition part (1) in a predetermined amount (generally from 0.1 to 2 mL). When the specimen-containing solution is added dropwise, the specimen-containing solution starts to migrate in the sample addition part (1).

The specimen sample used in the present invention is a specimen sample which may contain varicella-zoster virus which is a detection target, and specifically, a blister's fluid obtained by puncturing a blister of a patient infected with varicella-zoster virus, a pharyngeal swab, or the like is exemplified, but the specimen is not limited thereto.

(2) Step of Allowing Antibody or Antibody Fragment Thereof Retained in Labeling Substance Retaining Part to Recognize Varicella-Zoster Virus The step (2) is a step in which the specimen-containing solution added to the sample addition part in the step (1) is allowed to migrate to the labeling substance retaining part (2), and the antibody (first antibody) or an antibody fragment thereof to which a labeling substance retained in the labeling substance retaining part has bound is allowed to recognize glycoprotein E of varicella-zoster virus (VZVgE) which is the detection target in the specimen.

As the labeling substance, the above-mentioned substance can be used. The antibody (first antibody) or an antibody fragment thereof which binds to the labeling substance is an antibody or an antibody fragment thereof which recognizes VZVgE as described above. This antibody or an antibody fragment thereof recognizes and binds to VZVgE in the specimen developed from the sample addition part.

(3) Step of Developing Specimen and Antibody or Antibody Fragment Thereof in Chromatographic Medium Part as Mobile Phase The step (3) is a step in which after varicella-zoster virus which is the detection target is recognized by the antibody or an antibody fragment thereof to which the labeling substance has bound in the labeling substance retaining part in the step (2), the specimen and the antibody or an antibody fragment thereof are allowed to pass on the chromatographic medium part as a mobile phase.

(4) Step of Detecting Varicella-Zoster Virus in Developed Mobile Phase by Antibody or Antibody Fragment Thereof Contained in Detection Part The step (4) is a step in which VZVgE in varicella-zoster virus in the specimen having passed on the chromatographic medium part as the mobile phase is specifically reacted and bound so as to be interposed in a sandwich-like manner between the antibody or an antibody fragment thereof retained, that is, fixed on the detection part and the antibody or an antibody fragment thereof to which the labeling substance has bound in the step (2) by an antigen-antibody specific binding reaction, so that the detection part is colored.

The antibody (second antibody) or an antibody fragment thereof is an antibody or an antibody fragment thereof which recognizes VZVgE as described above. When the antibody (first antibody) or an antibody fragment thereof which binds to the labeling substance is any one of the above-mentioned antibodies (1a) to (1c) or an antibody fragment thereof, it is preferred to incorporate any one of the above-mentioned antibodies (2a) to (2c) or an antibody fragment thereof in the detection part.

Further, when the first antibody or an antibody fragment thereof is any one of the above-mentioned antibodies (2a) to (2c) or an antibody fragment thereof, it is preferred to incorporate any one of the above-mentioned antibodies (1a) to (1c) or an antibody fragment thereof in the detection part.

When varicella-zoster virus which is the detection target is not present, the labeling reagent dissolved in an aqueous component of the sample does not cause a specific binding reaction even if it passes through the detection part on the chromatographic medium part, and therefore, the detection part is not colored.

Finally, the aqueous component of the specimen-containing solution migrates to the absorption part (5).

<<Radioactive Material Labeled Immune Antibody Method>>

In the radioactive material labeled immune antibody method, for example, the antibody or the antibody fragment thereof of the present invention is allowed to react with an antigen or a cell expressing an antigen, or the like, and further allowed to react with an anti-immunoglobulin antibody or an antibody fragment thereof subjected to radiolabeling, followed by measurement with a scintillation counter or the like.

<<Enzyme Immunoassay Method>>

In the enzyme immunoassay method, for example, the antibody or the antibody fragment thereof of the present invention is allowed to react with an antigen or a cell expressing an antigen, or the like, and further allowed to react with an anti-immunoglobulin antibody or an antibody fragment thereof subjected to labeling with an enzyme or the like, followed by adding a substrate and measuring the absorbance of the reaction solution with an absorptiometer. For example, a sandwich ELISA method or the like is used. As a labeling substance used in the enzyme immunoassay method, a known [Enzyme Immunoassay Method, Igaku-Shoin Ltd. (1987)] enzyme label can be used.

For example, an alkaline phosphatase label, a peroxidase label, a luciferase label, a biotin label, or the like is used. The sandwich ELISA method is a method in which after an antibody is bound to a solid phase, an antigen that is a detection or measurement target is trapped, and then, a second antibody is allowed to react with the trapped antigen. In the ELISA method, two types of antibodies which are antibodies or antibody fragments that recognize the antigen desired to be detected or measured and which have different antigen recognition sites are prepared, and among these, a first antibody or antibody fragment is adsorbed on a plate (for example, a 96-well plate) in advance, and subsequently, a second antibody or antibody fragment is labeled with a fluorescent substance such as FITC, an enzyme such as peroxidase, or biotin, or the like beforehand. With the plate on which the antibody is adsorbed, cells or a homogenate thereof, tissues or a homogenate thereof, a cell culture supernatant, serum, pleural effusion, ascites, intraocular fluid, or the like separated from the living body is allowed to react, and thereafter, a labeled monoclonal antibody or antibody fragment is allowed to react, followed by a detection reaction according to the labeling substance. From a calibration curve created by serially diluting the antigen at a known concentration, the antigen concentration in the test sample is calculated. As the antibody used in the sandwich ELISA method, either a polyclonal antibody or a monoclonal antibody may be used, and an antibody fragment such as Fab, Fab' or $F(ab)_2$ may also be used. The combination of the two types of antibodies used in the sandwich ELISA method may be a combination of monoclonal antibodies or antibody fragments which recognize different epitopes or may be a combination of a polyclonal antibody and a monoclonal antibody or an antibody fragment.

<<Fluorescence Immunoassay Method>>

In the fluorescence immunoassay method, measurement is carried out by the method described in the documents [Monoclonal Antibodies-Principles and practice, Third edition, Academic Press (1996), Manual for monoclonal antibody experiments, Kodansha scientific books (1987)] or the like. As the labeling substance used in the fluorescence immunoassay method, a known [Fluorescent Antibody Method, Soft Science, Inc. (1983)] fluorescent label can be used. For example, FITC, RITC, or the like is used.

<<Luminescence Immunoassay Method>>

In the luminescence immunoassay method, measurement is carried out by the method described in the document [Bioluminescence and Chemiluminescence, Clinical Test 42, Hirokawa-Shoten Ltd. (1998)] or the like. As the labeling substance used in the luminescence immunoassay method, a known luminescent label is exemplified, and an acridinium ester, lophine, or the like is used.

<<Western Blotting Method>>

In the Western blotting method, after fractionating an antigen, cells expressing an antigen, or the like by SDS (sodium dodecyl sulfate)-PAGE (polyacrylamide gel) [Antibodies—A Laboratory Manual Cold Spring Harbor Laboratory (1988)], the gel is blotted on a polyvinylidene fluoride (PVDF) membrane or a nitrocellulose membrane, an antibody or an antibody fragment which recognizes the antigen is allowed to react with the membrane, and further, an anti-mouse IgG antibody or a binding fragment subjected to labeling with a fluorescent substance such as FITC, labeling with an enzyme such as peroxidase, biotin labeling, or the like is allowed to react therewith, and thereafter, the label is visualized, whereby measurement is carried out.

An example is shown below. Cells or tissues expressing a polypeptide having the amino acid sequence of SEQ ID NO: 2 are lysed, and 0.1 to 30 μg as a protein amount per lane is subjected to electrophoresis by the SDS-PAGE method under reducing conditions. The electrophoresed proteins are transferred to a PVDF membrane and allowed to react with PBS containing 1 to 10% BSA (hereinafter referred to as BSA-PBS) at room temperature for 30 minutes to perform a blocking operation. Here, the monoclonal antibody of the present invention is allowed to react, and the membrane is washed with PBS containing 0.05 to 0.1% Tween 20 (hereinafter referred to as Tween-PBS) and allowed to react with a goat anti-mouse IgG labeled with peroxidase at room temperature for 2 hours. By washing with Tween-PBS and detecting a band to which the monoclonal antibody is bound using ECL Western Blotting Detection Reagents (manufactured by Amersham, Inc.) or the like, the polypeptide having the amino acid sequence of SEQ ID NO: 2 is detected. As the antibody used for detection by Western blotting, an antibody capable of binding to a polypeptide which does not retain the natural conformation is used.

<<Physicochemical Method>>

The physicochemical method is carried out, for example, by binding VZVgE, which is the antigen, to the monoclonal antibody or the antibody fragment thereof of the present invention to form an aggregate and detecting the aggregate. As another physicochemical method, a capillary tube method, a one-dimensional immunodiffusion method, an immunoturbidimetric method, a latex immunoturbidimetric method [Outline of Clinical Examination Method, KANEHARA & Co., LTD. (1998)], or the like can also be used. In the latex immunoturbidimetric method, when a carrier such as a polystyrene latex having a particle size of about 0.1 to 1 μm sensitized with an antibody or an antigen is used to cause the antigen-antibody reaction with a corresponding antigen or antibody, the scattered light is increased in a reaction solution, and the transmitted light is decreased. The antigen concentration or the like in a test sample is measured by detecting this change as an absorbance or an integrating sphere turbidity.

For the detection or measurement of cells expressing VZVgE, a known immunological detection method can be used, but particularly, an immunoprecipitation method, an immunocytostaining method, an immunohistostaining method, a fluorescent antibody staining method, or the like is preferably used.

In the immunoprecipitation method, after allowing cells or the like expressing VZVgE to react with the monoclonal antibody or the antibody fragment thereof of the present invention, a carrier having a specific binding ability to an immunoglobulin such as Protein G-Sepharose is added thereto to precipitate an antigen-antibody complex. Alternatively, the method can also be carried out by the following method. The monoclonal antibody or the antibody fragment thereof of the present invention described above is immobilized on a 96-well plate for ELISA, followed by blocking with BSA-PBS. When the antibody is, for example, in an unpurified state such as a hybridoma culture supernatant, anti-mouse immunoglobulin, anti-rat immunoglobulin, protein A, protein G, or the like is immobilized on a 96-well plate for ELISA in advance, followed by blocking with BSA-PBS, and thereafter, the hybridoma culture supernatant is dispensed and bound thereto. Subsequently, BSA-PBS is discarded, and the plate is thoroughly washed with PBS, and then, a lysate solution of cells or tissues expressing VZVgE is allowed to react therewith. From the plate after being thoroughly washed, an immunoprecipitate is extracted with a sample buffer for SDS-PAGE, and then detected by the above-mentioned Western blotting.

The immunocytostaining method or the immunohistostaining method is a method in which cells or tissues expressing an antigen, or the like are treated with a surfactant or methanol, or the like for enhancing the permeability of the antibody in some cases, and then are allowed to react with the monoclonal antibody of the present invention, and further allowed to react with an anti-immunoglobulin antibody or a binding fragment thereof fluorescently labeled with FITC or the like, labeled with an enzyme such as peroxidase, or labeled with biotin, or the like, and thereafter, the label is visualized and then observed with a microscope. In addition, detection can be carried out by a fluorescent antibody staining method in which a fluorescently labeled antibody is allowed to react with a cell and analyzed with a flow cytometer [Monoclonal Antibodies-Principles and Practice, Third edition, Academic Press (1996), Monoclonal Antibody Experimental Manual, Kodansha scientific books (1987)]. In particular, the monoclonal antibody or the antibody fragment thereof of the present invention which binds to VZVgE enables detection of a cell which expresses the detection target while retaining the natural conformation by a fluorescent antibody staining method.

In addition, when the FMAT 8100 HTS system (manufactured by Applied Biosystems, Inc.) or the like is used in the fluorescent antibody staining method, the amount of an antigen or the amount of an antibody can be measured without separating the formed antibody-antigen complex from a free antibody or antigen that is not involved in the formation of the antibody-antigen complex.

<Immunological Measurement Kit>

An immunological measurement kit of the present invention includes the above-mentioned immunological measurement device, and a specimen diluent for diluting and developing a specimen (sometimes referred to as “specimen sample” or simply “sample”).

The specimen diluent in the immunological measurement kit of the present invention can also be used as a developing solution, but in general, water is used as a solvent, and a buffer solution, a salt, and a nonionic surfactant, and further, for example, one type or two or more types of a protein for promoting an antigen-antibody reaction or suppressing a nonspecific reaction, a polymeric compound (PVP or the like), an ionic surfactant or a polyanion, or an antimicrobial agent, a chelating agent, etc. may be added thereto.

Examples of the nonionic surfactant include Triton X-100 (trade name, polyethylene glycol mono-p-isooctylphenyl ether), Tween 20 (trade name, polyoxyethylene sorbitan monolaurate), NP-40 (trade name, Nonidet 40), Brij 35, and NONION MN-811 (manufactured by NOF CORPORATION), and one type or two or more types may be added.

Preferably, the nonionic surfactant contained in the specimen diluent includes one or more types of nonionic surfactants having an HLB value of 6 to 12. More preferably, it includes one or more types of nonionic surfactants having an HLB value of 7 to 11, and most suitably having an HLB value of 8 to 10. As the nonionic surfactant having an HLB value of 6 to 12, preferably, a polyoxyalkylene ether with a hydroxy group at one end is used. An alkyl group at one end may be linear or branched, and also an alkyl moiety of a repeating alkyl ether group may be linear or branched.

Further, it is more preferred that the nonionic surfactant contained in the specimen diluent not only includes one or more types of nonionic surfactants having an HLB value of 6 to 12, but also includes one or more types of nonionic surfactants having an HLB value of 13 to 18. As for the blending ratio thereof, the mass ratio of the total amount (B) of the nonionic surfactants having an HLB value of 13 to 18 to the total amount (A) of the nonionic surfactants having an HLB value of 6 to 12 is preferably as follows: A:B=30:70 to 70:30. More preferably, these nonionic surfactants are used at a blending ratio as follows: A:B=40:60 to 60:40.

Alternatively, in order to extract the detection target (VZVgE or the like) from the specimen sample in the specimen diluent, a known hydrophobic substance such as an alcohol may be incorporated in the specimen diluent or may be added thereto immediately after collecting the specimen. By incorporating or adding the hydrophobic substance in the specimen diluent, the detection target (VZVgE or the like) can be extracted from the specimen at the same time as when the specimen is diluted, and therefore, the time and labor for extraction in advance can be omitted, and also the detection sensitivity can be enhanced, and thus, this operation is preferred.

When the specimen diluent is used as a developing solution, a specimen-containing solution obtained by mixing the specimen sample and the developing solution in advance can be supplied and added dropwise onto the sample addition part to effect development, or the specimen sample is supplied and added dropwise onto the sample addition part in advance, and thereafter, the developing solution may be supplied and added dropwise onto the sample addition part to effect development.

Examples of a biological sample to be subjected to detection or measurement of VZVgE in the present invention include a tissue, a cell, blood, plasma, serum, pancreatic juice, urine, feces, a tissue fluid, a culture solution, and the like, and there is no particular limitation as long as a cell expressing VZVgE may be contained.

Hereinafter, the present invention will be further described by way of Examples, however, the invention is not limited to the following examples.

[Test Example 1] Preparation of Antibody Which Recognizes VZVgE

The amino acid sequence (SEQ ID NO: 1) of gE protein of VZV (VZVgE) was obtained from the DDBJ (the data base of the National Institute of Genetics). From the amino acid sequence of VZVgE, the amino acid sequence represented by SEQ ID NO: 2 (the amino acid sequence at positions 1 to 544 in the amino acid sequence represented by SEQ ID NO: 1), which is an extracellular domain excluding the transmembrane domain, was specified, and a gene sequence corresponding thereto was synthesized. After pET302/NT-His which is a His-tag expression vector was cleaved by the restriction enzyme EcoRI, the resulting fragments were treated with alkaline phosphatase as a dephosphorylation treatment, and then mixed with the above-synthesized gene sequence, and a ligation reaction was carried out using DNA Ligation Kit Ver. 2 (Takara Bio, Inc.).

A recombinant VZVgE plasmid integrated with a target gene was introduced into a recombinant protein expression host *E. coli* BL(DE3)pLysS (Novagen). A transformant was cultured on an LB agar plate culture medium, and an obtained colony was cultured in an LB liquid culture medium. Further, 1 mM IPTG (Takara Bio, Inc.) was added thereto to induce the expression of the recombinant VZVgE, and then, the *E. coli* was recovered. The recovered *E. coli* was resuspended in a lysate buffer [0.5% Triton X-100 (Sigma), 10 mM imidazole, 20 mM phosphate, and 0.5 M NaCl (pH 7.4) (Amersham)], and lysed by a sonication treatment, and then, the recombinant VZVgE was purified using His trap Kit (Amersham). The purified protein was dialyzed against phosphate buffered saline (hereinafter, referred to as "PBS"), and thus, the target recombinant VZVgE was prepared.

By using the obtained recombinant VZVgE as the immunization antigen, a monoclonal antibody against the recombinant VZVgE (hereinafter referred to as "anti-VZV gE antibody") was prepared. The preparation of the monoclonal antibody was carried out according to a conventional method as follows.

100 μg of the recombinant VZVgE was mixed with the same amount of Adjuvant Complete Freund (Difco), and a mouse (BALB/c, 5 weeks of age, Japan SLC, Inc.) was immunized with the mixture 3 times, and then, the spleen cells thereof were used for cell fusion.

For the cell fusion, Sp2/0-Ag14 cells (Shulman et al., Nature, 276, 269-270, 1978) which were mouse myeloma cells were used. In the culturing of the cells, a culture medium obtained by adding 0.3 mg/mL L-glutamine, 100 units/mL penicillin G potassium, 100 μg/mL streptomycin sulfate, and 40 μg/mL gentamicin to Dulbecco's modified Eagle medium (Gibco) (DMEM), and further adding fetal bovine serum (JRH) thereto to give a final concentration of 10% was used.

The cell fusion was performed by mixing the spleen cells of the immunized mouse with the Sp2/0-Ag14 cells, and adding a polyethylene glycol solution (Sigma) thereto. The resulting fused cells were cultured in HAT-DMEM [serum-supplemented DMEM containing 0.1 mM sodium hypoxanthine, 0.4 μM aminopterin, and 0.016 mM thymidine (Gibco)], and the production of the antibody in the culture supernatant was confirmed by the enzyme-linked immunoassay (ELISA).

The cells which were positive for the production of the antibody were cultured in HT-DMEM [serum-supplemented DMEM containing 0.1 mM sodium hypoxanthine and 0.16 mM thymidine], and further, the culturing was continued in the serum-supplemented DMEM.

The cloned cells were inoculated into the abdominal cavity of a mouse (BALB/c, Retire, Japan SLC, Inc.) into which 2,6,10,14-tetramethylpentadecane (Sigma) was injected in advance, and then, the ascites thereof was collected. The ascites was applied to a protein G column, whereby the monoclonal antibody was purified. Eventually, 23 clones of cells which produce a monoclonal antibody that recognizes VZVgE were obtained.

[Test Example 2] Screening of Cell which Produces Antibody that Recognizes Amino Acid Sequence at Positions 1 to 188 in Amino Acid Sequence of VZVgE In order to screen a cell which produces an antibody that recognizes the amino acid sequence at positions 1 to 188 in the amino acid sequence of VZVgE from the 23 clones of cells which produce a monoclonal antibody that recognizes VZVgE obtained in Test Example 1, the following experiment was performed.

A recombinant protein composed of the amino acid sequence at positions 1 to 188 in the amino acid sequence of VZVgE represented by SEQ ID NO: 1 was prepared in the same manner as in Test Example 1 and used in the following experiment.

A 0.01 mg/mL solution of the prepared VZVgE recombinant protein (the amino acid sequence at positions 1 to 188 in the amino acid sequence of SEQ ID NO: 1) was mixed with the same amount of 2× Tris-Glycine SDS Sample Buffer (manufactured by TEFCO) supplemented with 10% 2-mercaptoethanol, followed by heating at 100° C. for 10 minutes, and the resulting mixture was subjected to SDS-PAGE. The SDS-PAGE was performed according to a known standard method using Ready Gel J5-20% 12 well (manufactured by Bio-Rad, Inc.). A protein was transferred from the gel after electrophoresis to Sequi-Blot PVDF Membrane (manufactured by Bio-Rad, Inc.) using a blotting device (manufactured by Bio-Rad, Inc.). The PVDF membrane after transfer was blocked with ImmunoBlock (DS Pharma Laboratories) at room temperature for 1 hour.

The blocking solution was removed, and the PVDF membrane was washed with PBS containing 0.05% Tween 20 (trade name) (hereinafter, referred to as "T-PBS") for 10 minutes three times, then the resulting PVDF membrane was incubated at room temperature for 1 hour together with the culture supernatant containing the monoclonal antibody produced from each of the 23 clones of monoclonal antibody-producing cells obtained in Test Example 1. Each antibody was prepared at a concentration of 10 μg/mL and was allowed to react with the VZVgE recombinant protein in an amount of 1.0 Kg per lane.

After the PVDF membrane was washed with T-PBS for 10 minutes three times, the PVDF membrane was incubated at room temperature for 30 minutes together with alkaline phosphatase-labeled anti-mouse IgG (manufactured by Sigma, Inc.) diluted 5000-fold with T-PBS. After washing with T-PBS for 10 minutes three times, the PVDF membrane was incubated together with 1-Step™ NBT/BCIP (manufactured by Pierce, Inc.) that is a chromogenic substrate, whereby the antibody bound to the PVDF membrane was visualized.

As a result, a plurality of bands of 21 kDa (corresponding to the amino acid sequence at positions 1 to 188 of VZVgE) could be detected from the 23 monoclonal antibodies. Two types of antibodies were arbitrarily selected from the antibodies to be subjected to the below-mentioned immunochromatographic analysis test, and the hybridomas which produce the antibody were cloned, then, these two independent clones were selected and named Hybridomas A and B, respectively. Further, the antibodies which produce Hybridomas A and B were named Antibodies A and B, respectively. Both antibodies are antibodies which recognize the amino acid sequence at positions 1 to 188 in the amino acid sequence of VZVgE represented by SEQ ID NO: 1. The subclasses of the monoclonal antibodies obtained from the two hybridoma strains were both IgG1.

[Test Example 3] Immunochromatographic Analysis

In this test, an immunochromatographic analysis device using Antibody A or B obtained in Test Example 2 in either one of the labeling substance retaining part and the detection part was prepared, and an immunochromatographic analysis was performed.

<Preparation of Immunochromatographic Analysis Device>

(1) Preparation of Sample Addition Part

As a sample addition part, a non-woven fabric composed of glass fiber (manufactured by Millipore, Inc., 300 mm×30 mm) was used.

(2) Preparation of Labeling Substance Retaining Part

To 0.5 mL of a colloidal gold suspension (manufactured by Tanaka Kikinzoku Kogyo K.K., LC 40 nm), 0.1 mL of an antibody (either one of Antibodies A and B) diluted with a phosphate buffer solution (pH 7.4) to a concentration of 0.05 mg/mL was added, and the resulting mixture was left to stand at room temperature for 10 minutes.

Subsequently, 0.1 mL of a phosphate buffer solution (pH 7.4) containing 1 mass % bovine serum albumin (BSA) was added thereto, and the resulting mixture was left to stand at room temperature for an additional 10 minutes. Thereafter, the mixture was thoroughly stirred, and then centrifuged at 8000×g for 15 minutes. After removing the supernatant, 0.1 mL of a phosphate buffer solution (pH 7.4) containing 1 mass % BSA was added thereto. According to the above-mentioned procedure, a labeling substance solution was prepared.

A solution obtained by adding 300 μL of a 10 mass % trehalose aqueous solution and 1.8 mL of distilled water to 300 μL of the above-prepared labeling substance solution was added uniformly to a 12 mm×300 mm glass fiber pad (manufactured by Millipore, Inc.), followed by drying in a vacuum dryer, whereby a labeling substance retaining part was prepared.

(3) Preparation of Chromatographic Medium Part and Detection Part

As a membrane, a sheet composed of nitrocellulose (manufactured by Millipore, Inc., trade name: HF 120, 300 mm×25 mm) was used.

Subsequently, 150 μL of a solution obtained by diluting an antibody (either one of Antibodies A and B) with a phosphate buffer solution (pH 7.4) containing 5 mass % isopropyl alcohol to a concentration of 1.0 mg/mL was applied to a detection region (detection line) on the dried membrane in a line with a width of 1 mm in an amount of 1 μL/mm (25 μL, per sheet) using a dispenser for immunochromatography "XYZ 3050" (manufactured by BioDot, Inc.).

Further, in order to confirm whether or not a gold nanoparticle labeling reagent is developed or to confirm the developing speed, on the downstream of the detection region, a solution obtained by diluting a goat-derived antiserum having affinity in a wide range for the gold nanoparticle labeling substance with a phosphate buffer solution (pH 7.4) was applied to a control region (control line). Thereafter, the solution was dried at 50° C. for 30 minutes, and then dried overnight at room temperature, whereby a chromatographic medium part and a detection part were prepared.

(4) Preparation of Immunochromatographic Analysis Device

Subsequently, to a base material composed of a backing sheet, the sample addition part, the labeling substance retaining part, the chromatographic medium part having the detection part, and a non-woven fabric made of glass fiber as an absorption part for absorbing the developed sample and labeling substance were sequentially bonded. Then, the resulting material was cut to a width of 5 mm by a cutting machine, whereby an immunochromatographic analysis device was prepared. The length of the labeling substance retaining part in the sample development direction was set to 12 mm.

(5) Specimen Diluent

A 50 mM HEPES buffer solution (pH 7.5) containing a mixture of 1 mass % nonionic surfactant NP-40 (manufactured by Nacalai Tesque, Inc., trade name: Nonidet P-40, HLB value: 17.7) and Nonion MN-811 (manufactured by NOF CORPORATION, trade name: Nonion MN-811, HLB value: 8.3) at a mass ratio of 1:1 was prepared and used as a specimen diluent for diluting a specimen.

<Measurement>

The color development intensity in the detection part was measured when using the immunochromatographic analysis device prepared above using 0.01 μg/mL of the VZVgE (amino acid sequence at positions 1 to 188) recombinant protein prepared in Test Example 2 as the antigen. The antigen was diluted 100-fold with the above-prepared specimen diluent, and the resulting solution was used as a specimen sample.

Each of the above-prepared specimen samples in an amount of 150 μL was placed on the sample addition part of the immunochromatographic analysis device and developed, and the degree of color development (color development intensity) in the detection part was measured using an immunochromatographic reader (manufactured by Hamamatsu Photonics K.K., C10066-10/-50). The results are shown in Table 1.

TABLE 1

| | | Detection part side | |
|---|---|---|---|
| | | Antibody A | Antibody B |
| Labeling substance | Antibody A | 29 | 218 |
| retaining part side | Antibody B | 250 | 6 |

From the results shown in Table 1, it was found that by using an antibody which recognizes the amino acid sequence at positions 1 to 188 in the amino acid sequence of VZVgE in the immunochromatographic analysis device, VZV can be detected.

[Test Example 4] Screening of Antibody Which Recognizes Amino Acid Sequence at Positions 48 to 88 in Amino Acid Sequence of VZVgE In order to screen an antibody which recognizes the amino acid sequence at positions 48 to 88 in the amino acid sequence of VZVgE among the monoclonal antibodies against VZVgE obtained in Test Example 1, the following experiment was performed.

To a 96-well plate for ELISA, Nunc Immuno module (manufactured by Thermo Fisher Scientific, Inc., Code 469949), as VZVgE (amino acid sequence at positions 48 to 88), 100 μL of 4 ng/mL protein VZVgE (amino acid sequence at positions 48 to 88) in a 50 mM carbonate buffer at pH 9.5, the protein VZVgE being synthesized by a peptide solid-phase synthesis method which is a conventional peptide chemical synthesis method, and purified, was added, followed by incubation at 4° C. for 16 hours. After 16 hours, the gE solution was removed, and the well was washed three times with 300 μL of PBST (0.05% Tween 20 in PBS). The liquid remaining in the well was removed by tapping on a paper towel.

As a blocking solution, 300 μL of 5% BSA in PBST (BSA: manufactured by Oriental Yeast Co., Ltd.) was added, followed by incubation at 37° C. for 1 hour. Thereafter, the BSA solution was removed, and the well was washed three times with 300 μL of PBST (0.05% Tween 20 in PBS). The liquid remaining in the well was removed by tapping on a paper towel. As a primary antibody, 100 μL of an anti-VZV gE antibody at 5 μg/mL in a 50% blocking solution was added to the well, followed by incubation at 37° C. for 1 hour. Thereafter, the primary antibody solution was removed, and the well was washed three times with 300 μL of PBST (0.05% Tween 20 in PBS).

As a secondary antibody, 100 μL of anti-mouse IgG (H+L), Rabbit, IgG Whole, Peroxidase Conjugated (manufactured by Wako Pure Chemical Industries, Ltd., code: 014-17611) at 1 mg/mL was added to the well, followed by incubation at 37° C. for 1.5 hours. Thereafter, the BSA solution was removed, and the well was washed three times with 300 μL of PBST (0.05% Tween 20 in PBS), and the liquid remaining in the well was removed by tapping on a paper towel.

To the well, 100 μL of Sure Blue Reserve TMB Microwell Peroxidase Substrate (1-Component) (manufactured by KPL, Inc., code 53-00-01) was added as a chromogenic substrate, and allowed to react for 15 minutes, and then the reaction was stopped by adding 100 μL of 2 N sulfuric acid. Then, an absorbance at 450 nm was measured with a microplate reader (manufactured by Bio-Rad, Inc.).

As a result, six monoclonal antibodies could be isolated as the antibody which recognizes the amino acid sequence at positions 48 to 88 in the amino acid sequence of VZVgE. The hybridomas which produce the antibody were cloned, then, these six independent clones were selected and named Hybridomas 2, 3, 4, 5, 9, and 18, respectively. Further, the antibodies produced by Hybridomas 2, 3, 4, 5, 9, and 18 were named Antibodies 2, 3, 4, 5, 9, and 18, respectively. Further, the subclasses of the monoclonal antibodies obtained from the six hybridoma strains were all IgG1.

[Test Example 5] Immunochromatographic Analysis

In this test, an immunochromatographic analysis device using any of Antibodies 2, 3, 4, 5, 9, and 18 obtained in Test Example 4 was prepared, and an immunochromatographic analysis was performed.

<Preparation of Immunochromatographic Analysis Device>

(1) Preparation of Sample Addition Part

As a sample addition part, a non-woven fabric composed of glass fiber (manufactured by Millipore, Inc., 300 mm×30 mm) was used.

(2) Preparation of Labeling Substance Retaining Part

To 0.5 mL of a colloidal gold suspension (manufactured by Tanaka Kikinzoku Kogyo K.K., LC 40 nm), 0.1 mL of an antibody (any one of Antibodies 2, 3, 4, 5, 9, and 18) diluted with a phosphate buffer solution (pH 7.4) to a concentration of 0.05 mg/mL was added, and the resulting mixture was left to stand at room temperature for 10 minutes.

Subsequently, 0.1 mL of a phosphate buffer solution (pH 7.4) containing 1 mass % bovine serum albumin (BSA) was added thereto, and the resulting mixture was left to stand at room temperature for an additional 10 minutes. Thereafter, the mixture was thoroughly stirred, and then centrifuged at 8000×g for 15 minutes. After removing the supernatant, 0.1 mL of a phosphate buffer solution (pH 7.4) containing 1 mass % BSA was added thereto. According to the above-mentioned procedure, a labeling substance solution was prepared.

A solution obtained by adding 300 μL, of a 10 mass % trehalose aqueous solution and 1.8 mL of distilled water to 300 μL of the above-prepared labeling substance solution was added uniformly to a 12 mm×300 mm glass fiber pad (manufactured by Millipore, Inc.), followed by drying in a vacuum dryer, whereby a labeling substance retaining part was prepared.

(3) Preparation of Chromatographic Medium Part and Detection Part

As a membrane, a sheet composed of nitrocellulose (manufactured by Millipore, Inc., trade name: HF 120, 300 mm×25 mm) was used. Subsequently, 150 μL of a solution obtained by diluting an antibody (any one of Antibodies 2, 3, 4, 5, 9, and 18) with a phosphate buffer solution (pH 7.4) containing 5 mass % isopropyl alcohol to a concentration of 1.0 mg/mL was applied to a detection region (detection line) on the dried membrane in a line with a width of 1 mm in an amount of 1 μL/mm (25 μL per sheet) using a dispenser for immunochromatography "XYZ 3050" (manufactured by BioDot, Inc.).

Further, in order to confirm whether or not a gold nanoparticle labeling reagent is developed or to confirm the developing speed, on the downstream of the detection region, a solution obtained by diluting a goat-derived antiserum having affinity in a wide range for the gold nanoparticle labeling substance with a phosphate buffer solution (pH 7.4) was applied to a control region (control line). Thereafter, the solution was dried at 50° C. for 30 minutes, and then dried overnight at room temperature, whereby a chromatographic medium part and a detection part were prepared.

(4) Preparation of Immunochromatographic Analysis Device

Subsequently, to a base material composed of a backing sheet, the sample addition part, the labeling substance retaining part, the chromatographic medium part having the detection part, and a non-woven fabric made of glass fiber as an absorption part for absorbing the developed sample and labeling substance were sequentially bonded. Then, the resulting material was cut to a width of 5 mm by a cutting machine, whereby an immunochromatographic analysis device was prepared. The length of the labeling substance retaining part in the sample development direction was set to 12 mm.

(5) Specimen Diluent

A 50 mM HEPES buffer solution (pH 7.5) containing a mixture of 1 mass % nonionic surfactant NP-40 (manufactured by Nacalai Tesque, Inc., trade name: Nonidet P-40, HLB value: 17.7) and Nonion MN-811 (manufactured by NOF CORPORATION, trade name: Nonion MN-811, HLB value: 8.3) at a mass ratio of 1:1 was prepared and used as a specimen diluent for diluting a specimen.

<Measurement>

The color development intensity in the detection part was measured when using the immunochromatographic analysis device prepared above using 0.01 mg/mL of the VZVgE recombinant protein (CalBioreagents, Inc.) as the antigen. The antigen was diluted 100-fold with the above-prepared specimen diluent, and the resulting solution was used as a specimen sample.

Each of the above-prepared specimen samples in an amount of 150 μL was added onto the sample addition part of the immunochromatographic analysis device and developed, and the degree of color development (color development intensity) in the detection part was measured using an immunochromatographic reader (manufactured by Hamamatsu Photonics K.K., C10066-10/-50). The results are shown in Table 2.

TABLE 2

| | | Detection part side | | | | | |
|---|---|---|---|---|---|---|---|
| | | Antibody 9 | Antibody 2 | Antibody 3 | Antibody 4 | Antibody 5 | Antibody 18 |
| Labeling substance retaining part side | Antibody 9 | 29 | 39 | 53 | 5 | 52 | 218 |
| | Antibody 2 | 23 | 26 | 31 | 14 | 15 | 13 |
| | Antibody 3 | 65 | 23 | 35 | 19 | 11 | 32 |
| | Antibody 4 | 53 | 25 | 12 | 16 | 11 | 22 |
| | Antibody 5 | 25 | 15 | 38 | 36 | 20 | 134 |
| | Antibody 18 | 250 | 40 | 18 | 76 | 15 | 6 |

From the results shown in Table 2, it was found that by using an antibody which recognizes the amino acid sequence at positions 48 to 88 in the amino acid sequence of VZVgE in the immunochromatographic analysis device, VZV can be detected. In particular, it was found that when the antibodies (Antibodies 9 and 18) which recognize the amino acid sequence at positions 48 to 88 in the amino acid sequence of VZVgE were incorporated one by one in either the labeling substance retaining part or the detection part, VZV can be detected more strongly.

[Test Example 6] Sequence Analysis of Antibody Which Recognizes Amino Acid Sequence at Positions 48 to 88 in Amino Acid Sequence of VZVgE The amino acid sequences of Antibody 9 and Antibody 18, and the base sequences of DNAs encoding the amino acid sequences were determined. These results are shown in Table 3.

TABLE 3

| | Antibody 9 | Antibody 18 |
|---|---|---|
| Amino acid sequence of VH CDR1 | SEQ ID NO: 8 | SEQ ID NO: 14 |
| Amino acid sequence of VH CDR2 | SEQ ID NO: 9 | SEQ ID NO: 15 |
| Amino acid sequence of VH CDR3 | SEQ ID NO: 10 | SEQ ID NO: 16 |

TABLE 3-continued

| | Antibody 9 | Antibody 18 |
|---|---|---|
| Amino acid sequence of VL CDR1 | SEQ ID NO: 11 | SEQ ID NO: 17 |
| Amino acid sequence of VL CDR2 | SEQ ID NO: 12 | SEQ ID NO: 18 |
| Amino acid sequence of VL CDR3 | SEQ ID NO: 13 | SEQ ID NO: 19 |
| Amino acid sequence of VH | SEQ ID NO: 20 | SEQ ID NO: 22 |
| Amino acid sequence of VL | SEQ ID NO: 21 | SEQ ID NO: 23 |
| Base sequence of VH | SEQ ID NO: 24 | SEQ ID NO: 26 |
| Base sequence of VL | SEQ ID NO: 25 | SEQ ID NO: 27 |

The primers used in the analysis of the base sequences are as follows. In this connection, when using the primers included in Ig-Primer Sets (Novagen, Inc.) and the primers described in the document (IMMUNOTHERAPY, Vol. 33, 6, 2014), the base sequences encoding Antibody 9 and Antibody 18 were both not amplified. In SEQ ID NOS: 28 and 29, "r" represents a mixed base of a or g, "n" represents a mixed base of a, c, g, or t, "s" represents a mixed base of c or g, "m" represents a mixed base of a or c, and "w" represents a mixed base of a or t. Reverse Primer (SEQ ID NO: 28): 5'-cttccggaat tcsargtnma gctgsagsag tc-3', Reverse Primer SEQ ID NO: 29): 5'-cttccggaat tcsargtnma gctgsagsag tcwgg-3', Forward Primer (SEQ ID NO: 30): 5'-ggaagatcta tagacagatg ggggtgtcgt tttggc-3'

[Test Example 7] Immunochromatographic Analysis Using Actual Specimen

Test Example 5 was repeated except that as the specimen sample containing VZV, a blister's fluid of a person infected with VZV was used. The blister's fluid was collected by puncturing a blister of a test subject who is a person infected with VZV. Further, the collected blister's fluid was added to 500 μL of the above-prepared specimen diluent, and the resulting solution was used as the specimen sample.

Each of the above-prepared specimen samples in an amount of 150 μL was added onto the sample addition part of the immunochromatographic analysis device and developed, and the degree of color development (color development intensity) in the detection part was measured using an immunochromatographic reader (manufactured by Hamamatsu Photonics K.K., C10066-10/-50). As a result, also when the actual specimen was used as the test sample, the same results as in Test Example 5 in which the VZVgE recombinant protein was used as the antigen were obtained.

[Test Example 8] Epitope Analysis by Competitive Inhibition Test

In order to further analyze an epitope for an antibody, a peptide fragment composed of the amino acid sequence at positions 48 to 67 in the amino acid sequence of SEQ ID NO: 1 (Peptide 1, hereinafter abbreviated as P1), a peptide fragment composed of the amino acid sequence at positions 54 to 72 therein (Peptide 2, hereinafter abbreviated as P2), a peptide fragment composed of the amino acid sequence at positions 62 to 81 therein (Peptide 3, hereinafter abbreviated as P3), and a peptide fragment composed of the amino acid sequence at positions 69 to 88 therein (Peptide 4, hereinafter abbreviated as P4) were synthesized by the above-mentioned method. The analysis was carried out in the same manner as Test Example 5 except that the specimen diluent was added so that the concentration of each peptide fragment was as shown in Table 4. The positions of the respective peptide fragments in the full-length amino acid sequence of VZVgE are schematically shown in FIG. 2.

The results are shown in Table 4 and FIG. 3. In Table 4, PC denotes a control in which a synthetic peptide was not added. In Table 4 and FIG. 3, "NC" denotes a negative control, and shows a result of adding an antibody which reacts with VZVgE but does not react with the amino acid sequence at positions 48 to 88 in the amino acid sequence of SEQ ID NO: 1.

TABLE 4

| | | PC | P1 | P2 | P3 | P4 | NC |
|---|---|---|---|---|---|---|---|
| Color development intensity (mAbs) | 5 ng/mL | 690 | 726 | 697 | 677 | 596 | 624 |
| | 0.5 ng/mL | 136 | 136 | 127 | 128 | 149 | 155 |

As shown in Table 4, although a relatively excessive amount of the peptide fragment was added, competitive inhibition did not occur with any of the peptide fragments as compared with the VZVgE recombinant protein. Accordingly, it was found that the antibody reacts with the peptide fragment having the amino acid sequence at positions 48 to 88 in the amino acid sequence of SEQ ID NO: 1, but does not react with the peptide fragment at positions 48 to 67 (P1), the peptide fragment at positions 54 to 72 (P2), the peptide fragment at positions 62 to 81 (P3), and the peptide fragment at positions 69 to 88 (P4).

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

REFERENCE SIGNS LIST

1. sample addition part (sample pad)
2. labeling substance retaining part
3. chromatographic medium part
4. detection part
5. absorption part
6. backing sheet

The invention claimed is:

1. An immunological measurement device for detecting Varicella-zoster virus (VZV), comprising a sample addition part, a labeling substance retaining part, a chromatographic medium part having a detection part, and an absorption part, and wherein the labeling substance retaining part and the detection part are the following (i) or (ii):

(i) the labeling substance retaining part contains a labeling substance and an antibody of (1a) below bound to the labeling substance, and the detection part contains an antibody of (2a) below; or (ii) the labeling substance retaining part contains a labeling substance and an antibody of (2a) below bound to the labeling substance, and the detection part contains an antibody of (1a) below:

(1a) an antibody in which the amino acid sequences of CDRs 1 to 3 of VH contain the amino acid sequences represented by SEQ ID NOS: 8, 9, and 10, respectively, and the amino acid sequences of CDRs 1 to 3 of VL contain the amino acid sequences represented by SEQ ID NOS: 11, 12, and 13, respectively;

(2a) an antibody in which the amino acid sequences of CDRs 1 to 3 of VH of the antibody contain the amino acid sequences represented by SEQ ID NOS: 14, 15, and 16, respectively, and the amino acid sequences of CDRs 1 to 3 of VL of the antibody contain the amino acid sequences represented by SEQ ID NOS: 17, 18, and 19, respectively.

2. The immunological measurement device according to claim 1, wherein a sample to be added to the sample addition part is a blister's fluid containing varicella-zoster virus.

* * * * *